US010107753B2

(12) United States Patent
Betzig et al.

(10) Patent No.: US 10,107,753 B2
(45) Date of Patent: *Oct. 23, 2018

(54) OPTICAL MICROSCOPY WITH PHOTOTRANSFORMABLE OPTICAL LABELS

(71) Applicant: Hestzig LLC, Ashburn, VA (US)

(72) Inventors: Robert Eric Betzig, Ashburn, VA (US); Harald F. Hess, Leesburg, VA (US)

(73) Assignee: Hestzig LLC, Ashburn, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/170,521

(22) Filed: Jun. 1, 2016

(65) Prior Publication Data

US 2017/0115221 A1    Apr. 27, 2017

Related U.S. Application Data

(63) Continuation of application No. 14/064,582, filed on Oct. 28, 2013, now Pat. No. 9,360,426, which is a (Continued)

(51) Int. Cl.
*G01N 21/64* (2006.01)
*G01N 33/58* (2006.01)
(Continued)

(52) U.S. Cl.
CPC ..... *G01N 21/6428* (2013.01); *G01N 21/6458* (2013.01); *G01N 33/582* (2013.01); (Continued)

(58) Field of Classification Search
CPC ... G01N 2021/6439; G01N 2021/6441; G01N 2021/6421; G01N 2021/6419; G01N 21/64; G01N 21/6428; G01N 33/582
See application file for complete search history.

(56) References Cited

U.S. PATENT DOCUMENTS 5,731,588 A    3/1998    Hell
5,866,911 A    2/1999    Baer
(Continued)

FOREIGN PATENT DOCUMENTS

DE    4416558 C2    8/1995
EP    1892517 A2    2/2008
(Continued)

OTHER PUBLICATIONS

S.W. Hell, S. Jakobs, L. Kastrup, "Imaging and writing at the nanoscale with focused visible light through saturable optical transitions" Applied Physics A, 2003, vol. 77, No. 7, pp. 859-860.*
(Continued)

*Primary Examiner* — Dominic J Bologna
(74) *Attorney, Agent, or Firm* — Brake Hughes Bellermann LLP

(57) ABSTRACT

Imaging a sample that includes phototransformable optical labels ("PTOLs") with an optical system having a diffraction-limited resolution volume (DLRV), includes providing activation radiation to the PTOLs to activate a statistical subset of the PTOLs. A density of the PTOLs of the activated subset is less than an inverse of the DLRV. Excitation radiation is provided to the activated subset to excite activated PTOLs. Radiation emitted from the activated and excited PTOLs located at different focal planes of the optical system within the sample is detected with the optical system. The preceding steps are repeated one or more times, each time activating a different statistical subset of the plurality of PTOLs. Three-dimensional locations within the sample are determined, with a sub-diffraction-limited accuracy, of the activated and excited PTOLs based on the radiation emitted from the activated and excited PTOLs that is detected from the different focal planes of the optical system.

28 Claims, 20 Drawing Sheets

Related U.S. Application Data continuation of application No. 13/655,102, filed on Oct. 18, 2012, now Pat. No. 8,599,376, which is a continuation of application No. 12/956,946, filed on Nov. 30, 2010, now Pat. No. 8,462,336, which is a continuation of application No. 12/645,019, filed on Dec. 22, 2009, now Pat. No. 7,864,314, which is a continuation of application No. 11/944,274, filed on Nov. 21, 2007, now Pat. No. 7,782,457, which is a continuation of application No. PCT/US2006/019887, filed on May 23, 2006.

(60) Provisional application No. 60/780,968, filed on Mar. 10, 2006, provisional application No. 60/683,337, filed on May 23, 2005.

(51) Int. Cl.
G02B 21/16 (2006.01)
G02B 21/36 (2006.01)

(52) U.S. Cl.
CPC ........... *G02B 21/16* (2013.01); *G02B 21/367* (2013.01); *G01N 2021/6419* (2013.01); *G01N 2021/6439* (2013.01); *G01N 2021/6441* (2013.01)

(56) References Cited

U.S. PATENT DOCUMENTS

| | | | |
|---|---|---|---|
| 5,952,668 A | 9/1999 | Baer | |
| 6,259,104 B1 | 7/2001 | Baer | |
| 6,388,788 B1 | 5/2002 | Harris et al. | |
| 6,537,829 B1 | 3/2003 | Zarling et al. | |
| 6,633,432 B2 | 10/2003 | Iketaki | |
| 6,667,830 B1 | 12/2003 | Iketaki | |
| 6,844,150 B2 | 1/2005 | Weiss | |
| 6,844,963 B2 | 1/2005 | Iketaki | |
| 6,859,313 B2 | 2/2005 | Iketaki | |
| 7,064,824 B2 | 6/2006 | Hell | |
| 7,071,477 B2 | 7/2006 | Baer | |
| 7,298,476 B2 | 11/2007 | Tsai | |
| 7,394,077 B2 | 7/2008 | Baer | |
| 7,408,176 B2 | 8/2008 | Goodwin | |
| 7,430,045 B2 | 9/2008 | Hell | |
| 7,535,012 B2 | 5/2009 | Betzig et al. | |
| 7,619,732 B2 | 11/2009 | Gugel | |
| 7,626,694 B2 * | 12/2009 | Betzig ................ | G01N 21/6458 250/458.1 |
| 7,626,695 B2 | 12/2009 | Betzig et al. | |
| 7,626,703 B2 | 12/2009 | Betzig et al. | |
| 7,710,563 B2 | 5/2010 | Betzig et al. | |
| 7,776,613 B2 | 8/2010 | Zhuang et al. | |
| 7,782,457 B2 * | 8/2010 | Betzig ................ | G01N 21/6458 356/317 |
| 7,803,634 B2 | 9/2010 | Klimove et al. | |
| 7,864,314 B2 | 1/2011 | Hess | |
| 8,462,336 B2 | 6/2013 | Hess et al. | |
| 8,599,376 B2 | 12/2013 | Betzig et al. | |
| 9,360,426 B2 * | 6/2016 | Betzig ................ | G01N 21/6458 |
| 2001/0045523 A1 | 11/2001 | Baer | |
| 2001/0045529 A1 | 11/2001 | Iketaki et al. | |
| 2002/0020819 A1 | 2/2002 | Wolleschensky | |
| 2002/0098516 A1 | 7/2002 | Cosgrove | |
| 2003/0092884 A1 | 5/2003 | Lukyanov et al. | |
| 2003/0175809 A1 | 9/2003 | Fradkov et al. | |
| 2004/0110206 A1 | 6/2004 | Wong | |
| 2004/0191915 A1 | 9/2004 | Bawendi | |
| 2006/0038993 A1 | 2/2006 | Hell | |
| 2007/0096038 A1 | 5/2007 | Tsai et al. | |
| 2008/0068589 A1 | 3/2008 | Hess et al. | |
| 2008/0070322 A1 | 3/2008 | Hess et al. | |
| 2008/0070323 A1 | 3/2008 | Hess et al. | |
| 2008/0111086 A1 | 5/2008 | Betzig et al. | |
| 2008/0182336 A1 | 7/2008 | Zhuang | |
| 2009/0045353 A1 | 2/2009 | Alexeevich et al. | |
| 2009/0135432 A1 | 5/2009 | Betzig | |
| 2009/0206251 A1 | 8/2009 | Hess et al. | |
| 2010/0181497 A1 | 7/2010 | Hess | |
| 2011/0102787 A1 | 5/2011 | Hess | |
| 2013/0126759 A1 | 5/2013 | Betzig et al. | |
| 2014/0287941 A1 | 9/2014 | Betzig et al. | |

FOREIGN PATENT DOCUMENTS

| | | |
|---|---|---|
| EP | 1894010 B1 | 2/2013 |
| JP | 2001272343 A | 10/2001 |
| JP | 2001272343 A2 | 10/2001 |
| JP | 2003-015048 | 1/2003 |
| JP | 2003015048 A | 1/2003 |
| JP | 2003015048 A2 | 1/2003 |
| JP | 2004-521323 | 7/2004 |
| JP | 2004521323 A | 7/2004 |
| JP | 2004521323 T2 | 7/2004 |
| JP | 2011-39065 A | 2/2011 |
| JP | 4709278 | 3/2011 |
| WO | 2006/123967 | 9/2000 |
| WO | 0196373 A2 | 12/2001 |
| WO | 2002044412 A1 | 6/2002 |
| WO | 2003031951 A1 | 4/2003 |
| WO | 2004/090617 A2 | 10/2004 |
| WO | 2004090617 A2 | 10/2004 |
| WO | 2004090617 A2 | 10/2004 |
| WO | 2004090950 A2 | 10/2004 |
| WO | 10325460 A1 | 11/2004 |
| WO | 04109286 A2 | 12/2004 |
| WO | 2006/058187 A3 | 11/2006 |
| WO | 2006058187 A3 | 11/2006 |
| WO | 2006123967 A2 | 11/2006 |
| WO | 2006127692 A2 | 11/2006 |
| WO | 2006127692 A3 | 11/2006 |
| WO | 2006/127692 A3 | 4/2007 |
| WO | 2002016911 A1 | 2/2012 |

OTHER PUBLICATIONS

Toward fluorescence nanoscopy, Stefan W Hell, Nature Biotechnology 21, 1347-1355 (2003) Oct. 31, 2003.*
Notice of Allowance for U.S. Appl. No. 14/064,582, dated Apr. 20, 2016, 9 Pages.
Response to Non-Final Office Action for U.S. Appl. No. 14/064,582, filed Mar. 13, 2015, 8 pages.
Response to Notice of Non-Compliant Amendment for U.S. Appl. No. 14/064,582, filed Oct. 19, 2015, 10 pages.
Office Action for Japanese Patent Application No. 2008513618, dated Jun. 10, 2010, 12 pages.
Office Action for Japanese Patent Application No. 2008513618, dated Sep. 28, 2009, 17 pages.
Office Action for JP Application No. 2012-271526, dated Jul. 29, 2014, 3 Pages.
Office Action for JP Patent Application No. 2008-513618, dated Aug. 10, 2009, 13 pages.
Office Action Response for JP Application No. 2012-271526, filed Mar. 17, 2014, 6 Pages.
Office Action for Canadian Patent Application No. 2609653, dated Jan. 26, 2011.
Ando, et al., "An optical marker based on the UV-induced green-to-red photoconversion of a fluorescent protein", PNAS, vol. 99, No. 20, 2002, pp. 12651-12656.
Ando, et al., "Regulated Fast Nucleocytoplasmic Shutting Observed by Reversible Protein Highlighting", Science, vol. 306, No. 5700, Nov. 19, 2004, 5 pages.
Hofmann, et al., "Breaking the diffraction barrier in Fluorescence misroscopy at low light intensities by using reversibly photoswitchable proteins", Proceedings of the National Academy of Sciences of USA,102(49), Dec. 6, 2005, pp. 17565-17569.
Notice of Allowance for Japanese Patent Application No. 2008-513618, dated Feb. 22, 2011, 4 pages.
Notice of Allowance for JP Application No. 2012-271526, dated Feb. 17, 2015, 3 pages.

(56) References Cited

OTHER PUBLICATIONS

Hess, et al., "Near-Field Spectroscopy of the Quantum Constituents of a Luminescent System", Science, vol. 264, Jun. 17, 1994, pp. 1740-1745.
Axelrod, "Total Internal Reflection Fluorescence Microscopy", Methods Cell Biol. 30, 1989, pp. 245-270.
Betzig, "Excitation Strategies for Optical Lattice Microscopy", Optics Express, 13(8), Apr. 18, 2005, pp. 3021-3036.
Betzig, et al., "Near-Field Optics: Microscopy, Spectroscopy, and Surface Modification Beyond the Diffraction Limit.", Science, vol. 257, Jul. 10, 1992, pp. 189-195.
Betzig, "Proposed method for molecular optical imaging", Optics Letters/ vol. 20, No. 3, Feb. 1, 1995, pp. 237-239.
Betzig, et al., "Single Molecules Observed by Near-Field Scanning Optical Microscopy", Science, vol. 262, Nov. 26, 1993, pp. 1422-1425.
Cheezum, et al., "Quantitative Comparison of Algorithms for Tracking Single Fluorescent Particles", Biophysical Journal, vol. 81, Oct. 2001, pp. 2378-2388.
Chen, et al., "Site-specific labeling of proteins with small molecules in live cells", www.sciencedirect.com. Current Opinion in Biotechnology ,16:, 2005, pp. 35-40.
Chudakov, et al., "Kindling fluorescent proteins for precise in vivo photolabeling", www.nature.com/naturebiotechnology, vol. 21, nature biotechnology, Feb. 2003, pp. 191-194.
Chudakov, et al., "Photoswitchable cyan fluorescent protein for protein tracking", Nature Biotechnology, vol. 22, No. 11, Nov. 2004, pp. 1435-1439.
Churchman, et al., "Single molecule high-resolution colocalization of Cy3 and Cy5 attached to macromolecules measures intramolecular distances through time", www.pnas.org/cgi/doi/10.1073/pnas.0409487102, Feb. 1, 2005, pp. 1419-1423.
Cole, "Diffusional Mobility of Golgi Proteins in Membranes of Living Cells", Science, vol. 273, Aug. 9, 1996, pp. 797-801.
Eisenstein, "New fluorescent protein includes handy on-off switch", Nature Methods, 2(1), Jan. 2005, pp. 8-9.
European Application Serial No. 06784461.3, Office Action dated Sep. 21, 2010, 6 pages.
Notice of Opposition for EP Application No. 06784461.3, dated Nov. 27, 2013, 14 pages.
Response to Notice of Opposition for EP Application No. 06784461.3, filed May 27, 2014, 10 pages.
Summons to Attend Oral Proceedings for EP Application No. 06784461.3, dated Nov. 11, 2014, 11 pages.
Examination Notification Art. 94(3) for EP Application No. 11181556.9, dated Dec. 18, 2014, 5 Pages.
Examination Notification Art. 94(3) Response for EP Application No. 11181556.9, filed Jun. 26, 2015, 9 Pages.
Examination Notification Art. 94(3) for EP Application No. 111815571, dated Dec. 18, 2014, 5 Pages.
Examination Notification Art. 94(3) Response for EP Application No. 111815571, filed Jun. 26, 2015, 5 Pages.
Examination Notification Art. 94(3) for EP Application No. 11181561.9, dated Dec. 18, 2014, 6 Pages.
Examination Notification Art. 94(3) Response for EP Application No. 11181561.9, filed Jun. 29, 2015, 42 Pages.
Office Action for EP Application No. 11181561.9, dated Oct. 19, 2015, 6 pages.
Examination Notification Art. 94(3) for EP Application No. 11181563.5, dated Dec. 18, 2014, 5 Pages.
Examination Notification Art. 94(3) Response for EP Application No. 11181563.5, Filed Jun. 26, 2015, 5 Pages.
Examination Notification Art. 94(3) for EP Application No. 11181564.3, dated Dec. 18, 2014, 5 Pages.
Examination Notification Art. 94(3) Response for EP Application No. 11181564.3, Filed Jun. 29, 2015, 28 Pages.
Frohn, et al., "True optical resolution beyond the Rayleigh limit achieved by standing wave illumination", PNAS, vol. 37, No. 13, Jun. 20, 2000, pp. 7232-7236.
Gordon, et al., "Single-molecule high-resolution imaging with photobleaching", PNAS, vol. 101, No. 17, Apr. 27, 2004, pp. 6462-6465.
Gustafsson, "Surpassing the lateral resolution limit by a factor of two using structured illumination microscopy", Journal of Microscopy, vol. 198, Pt 2, May 2000, pp. 82-87.
Hell, et al., "Concepts for nanoscale resolution in fluorescence microscopy", Current Opinion in Neurobiology, vol. 14, No. 5, Oct. 2004, 11 pages.
Hell, et al., "Imaging and writing at the nanoscale with focused visible light through Saturable optical transitions", Applied Physics A, Aug. 1, 2003, 3 pages.
Hell, et al., "Ground-State-Depletion Fluorscence Microscopy: A Concept for Breaking the Diffraction Resolution Limit", Applied Physics B, 1995, pp. 495-497, 1995, pp. 495-497.
Hell, "Strategy for far-field optical imaging and writing without diffraction limit", Physics Letters A, North-Holland Publishing Co., Amsterdam, NL, vol. 326 No. 1-2, May 31, 2004, pp. 140-145.
Hell, "Toward fluorescence nanoscopy", Nature Biotechnology, Nature Publishing Group, New York, NY, US, vol. 21(11), Oct. 31, 2003, pp. 1347-1355.
Office Action Response for JP Application No. 2012-271526, filed Jan. 23, 2015, 13 Pages.
Lidke, "Superresolution by localization of quantum dots using blinking statistics", Optics Express/ vol. 13, No. 18, Sep. 5, 2005, pp. 7052-7062.
Lukyanov, et al., "Natural animal coloration can be determined by a nonfluorescent green fluorescent protein homolog", Journal of Biology Chemistry, 275(34), Aug. 25, 2000, 25879-25882.
Lukyanov, et al., "Photoactivatable fluorescent proteins", Nature Reviews. Molecular Cell Biology, vol. 6, Nov. 2005, pp. 885-891.
Matsumoto, et al., "Localization of Human Immunodeficiency Virus Type 1 Gag and Env at the Plasma Membrane by Confocal Imaging", jvi.asm.org. vol. 74, 2000, pp. 8670-8679.
Moerner, "High-Resolution Optical Spectroscopy of Single Molecules in Solids", Acc. Chem. Res., vol. 29, No. 12, 1996, pp. 563-571.
Patterson, et al., "A Photoactivatable GFP for Selective Photolabeling of Proteins and Cells", www.sciencemag.org. Science, vol. 297, Sep. 13, 2002, pp. 1873-1877.
International Preliminary Report on Patentability for PCT Application No. PCTUS2006/019887, dated Dec. 6, 2007, 10 pages.
International Preliminary Report on Patentability for PCT Patent Application No. PCTUS2006/019887, dated Feb. 28, 2007, 10 pages.
International Search Report and Written Opinion for PCT Application No. PCTUS2006/019887, dated Feb. 28, 2007, 14 pages.
Politz, "Use of caged fluorochromes to track macromolecular movement in living cells", trends in Cell Biology (vol. 9), Jul. 1999, pp. 284-287.
Qu, et al., "Nanometer-localized multiple single-molecule fluorescence microscopy", PNAS. vol. 101. No. 31, Aug. 3, 2004, pp. 11298-11303.
Satoshi, et al., "Reversible Single-molecule photoswitching in the GFP-like fluorescent protein dronpa", Sciences of USA, 102(27), Jul. 5, 2005, pp. 9511-9516.
Schwartz, et al., "Development and Use of Fluorescent Protein Markers in Living Cells", www.sciencemag.org Science vol. 300, Apr. 4, 2003, pp. 87-91.
Thompson, et al., "Precise Nanometer Localization Analysis for Individual Fluorescent Probes", Biophysical Journal 32(5), May 2002, pp. 2775-2783.
Tsutsui, et al., "Semi-rational engineering of a coral fluorescent protein into an efficient highlighter", EMBO reports vol. 6, No. 3, 2005, pp. 233-238.
Westphal, et al., "Nanoscale Resolution in the Focal Plane of an Optical Microscope", PRL 94, 143903, Apr. 1, 2005, pp. 143903-1 to 143903-4.
Van Oijen, et al., "Far-field fluorescence microscopy beyond the diffraction limit", J. Opt. Soc. Am. A / vol. 16, No. 4/, Apr. 1999, pp. 909-915.

(56) References Cited

OTHER PUBLICATIONS

Westphal, et al., "Stimulated Emission Depletion Microscopy on Lithographic Nanostructures", J. Phys. B, vol. 38, 2005, pp. 695-705, 2005, pp. 695-705.
Wiedenmann, et al., "EosFP, a fluorescent marker protein with UV-inducible green-to-red fluorescence conversion", PNAS, vol. 101, No. 45, Nov. 9, 2004, pp. 15905-15910.
Yildiz, et al., "Myosin V Walks Hand-Over-Hand: Single Fluorophore Imaging with 1.5-nm Localization", www.sciencemag.org. Science vol. 300, Jun. 27, 2003, pp. 2061-2065.
Intenational Preliminary Report on Patentability for PCT Application No. PCTUS2006/019887, dated Dec. 6, 2007, 10 pages.
International Preliminary Report on Patentability for PCT Patent Applicaiton No. PCTUS2006/019887, dated Feb. 28, 2007, 10 pages.
Politz, "Use of caged fluorochromes to track macromolecular movement in living cells", trends in Cell Biology (vol. 9), Jul. 1999, 284-287.
Qu, et al., "Nanometer-localized multiple single-molecule fluorescence microscopy", PNAS. vol. 101. No. 31, Aug. 3, 2004, 11298-11303.
Satoshi, et al., "Reversible Single-molecule photoswitching in the GFP-like fluorescent protein dronpa", Sciences of USA, 102(27), Jul. 5, 2005, 9511-9516.
Schwartz, et al., "Development and Use of Fluorescent Protein Markers in Living Cells", www.sciencemag.org Science vol. 300, Apr. 4, 2003, 87-91.
Thompson, et al., "Precise Nanometer Localization Analysis for Individual Fluorescent Probes", Biophysical Journal 82(5), May 2002, 2775-2783.
Tsutsui, et al., "Semi-rational engineering of a coral fluorescent protein into an efficient highlighter", EMBO reports vol. 6, No. 3, 2005, 233-238.
Van Oijen, et al., "Far-field fluorescence microscopy beyond the diffraction limit", J. Opt. Soc. Am. A / vol. 16, No. 4/, Apr. 1999, 909-915.
Westphal, et al., "Nanoscale Resolution in the Focal Plane of an Optical Microscope", PRL 94, 143903, Apr. 1, 2005, 143903-1 to 143903-4.
Westphal, et al., "Stimulated Emission Depletion Microscopy on Lithographic Nanostructures", J. Phys. B, vol. 38, 2005, pp. 695-705, 2005, 695-705.
Wiedenmann, et al., "EosFP, a fluorescent marker protein with UV-inducible green-to-red fluorescence conversion", PNAS, vol. 101, No. 45, Nov. 9, 2004, 15905-15910.
Yildiz, et al., "Myosin V Walks Hand-Over-Hand: Single Fluorophore Imaging with 1.5-nm Localization", www. sciencemag.org. Science vol. 300, Jun. 27, 2003, 2061-2065.
EP Application No. 06784461.3, Office Action Response filed Mar. 21, 2011, 8 Pages.
EP Application No. 11181556.9, Examination Notification Art. 94(3) dated Feb. 25, 2013, 22 pages.
EP Application Serial No. 11181561.9, Examination Notification Art. 94(3) dated Feb. 25, 2013, 5 pages.
EP Application Serial No. 11181563.5, Examination Notification Art. 94(3) dated Feb. 25, 2013, 22 pages.
U.S. Appl. No. 12/956,946, Final Office Action dated Apr. 18, 2012, 10 pages.
U.S. Appl. No. 12/956,946, Notice of Allowance dated Oct. 26, 2012, 8 pages.
U.S. Appl. No. 12/956,946, Notice of Allowance dated Feb. 8, 2013, 7 pages.
U.S. Appl. No. 12/956,946, Non-Final Office Action dated Mar. 11, 2011, 19 pages.
U.S. Appl. No. 13/655,102, Notice of Allowance dated Jul. 30, 2013, 12 pages.
CA Application Serial No. 2,609,653, Notice of Allowance dated May 21, 2013, 1 page.
EP Application Serial No. 11181557.7, Examination Notification Art. 94(3) Response filed Aug. 28, 2013, 14 pages.
EP Application Serial No. 11181557.7, Examination Notification Art. 94(3) Response filed Feb. 25, 2013, 4 pages.
EP Application Serial No. 11181561.9, Examination Notification Art. 94(3) Response filed Sep. 4, 2013, 24 pages.
EP Application Serial No. 11181563.5, Examination Notification Art. 94(3) Response filed Aug. 28, 2013, 17 pages.
EP Application Serial No. 11181564.3, Examination Notification Art. 94(3) Response Filed Sep. 4, 2013, 21 pages.
EP Application Serial No. 11181564.3, Examination Notification Art. 94(3) dated Feb. 25, 2013, 7 pages.
JP Application Serial No. 2010-189163, Notice of Allowance dated Jul. 16, 2013, 4 pages.
JP Application Serial No. 2012-271526, Office Action dated Sep. 17, 2013, 3 pages.
European Search Report for EP Application No. 06784461.3-2204, dated Nov. 27, 2008, 15 pages.
JP Application Serial No. 2010-189163, Office Action dated Jun. 12, 2012, 4 pages.
Extended European Search Report for European Patent Application No. 11181556.9, dated Apr. 16, 2012, 13 pages.
Response to Final Office Action for U.S. Appl. No. 12/956,946, filed Oct. 17, 2012, 9 pages.
Response to Non Final Office Action for U.S. Appl. No. 12/956,946, filed Sep. 12, 2011, 7 pages.
Response to Office Action for EP Application No. 11181556.9, filed Aug. 28, 2013, 14 pages.
Office Action for European Patent Application No. 06784461.3, dated Sep. 8, 2009, 7 pages.
Extended European Search Report for EP Application No. 067844613, dated Nov. 27, 2008, 19 pages.
Extended European Search Report Response for EP Application No. 067844613, filed on Jun. 3, 2009, 4 pages.
U.S. Appl. No. 11/944,274, Ex parte Quale dated Apr. 12, 2010, 21 pages.
U.S. Appl. No. 11/944,274, Notice of Allowance dated Jul. 2, 2010, 23 pages.
Notice of Allowance for U.S. Appl. No. 11/944,274, dated Jul. 2, 2010, 8 pages.
Notice of Allowance for U.S. Appl. No. 11/944,280, dated Jun. 17, 2009, 22 pages.
Extended European Search Report for European Patent Application No. 11181557.7, dated Apr. 16, 2012, 13 pages.
Notice of Allowance for U.S. Appl. No. 11/944,280, dated Oct. 29, 2009, 6 pages.
Extended European Search Report for EP Application No. 11181561.9, dated Apr. 16, 2012, 12 pages.
Notice of Allowance for U.S. Appl. No. 11/944,280, dated Sep. 30, 2009, 17 pages.
Extended European Search Report for EP Application No. 11181563.5, dated Apr. 16, 2012, 15 pages.
Notice of Allowance for U.S. Appl. No. 11/944,285, dated Dec. 15, 2009, 10 pages.
Office Action for U.S. Appl. No. 11/944,285, dated Jun. 19, 2009, 18 pages.
Notice of Allowance for U.S. Appl. No. 11/944,289, dated Jul. 16, 2009, 12 pages.
Notice of Allowance for U.S. Appl. No. 11/944,289, dated Oct. 20, 2009, 10 pages.
Notice of Allowance for U.S. Appl. No. 11/944,289, dated Oct. 29, 2009, 10 pages.
Notice of Allowance for U.S. Appl. No. 11/944,289, dated Apr. 23, 2009, 15 pages.
Notice of Allowance for U.S. Appl. No. 11/944,312, dated Mar. 2, 2009, 15 pages.
Office Action for U.S. Appl. No. 11/944,312, dated Nov. 6, 2008, 20 pages.
Notice of Allowance for U.S. Appl. No. 11/944,321, dated Jul. 23, 2009, 30 pages.
Allowance for U.S. Appl. No. 11/944,321, dated Nov. 3, 2009, 11 pages.
Extended European Search Report for EP Application No. 11181564.3, dated Apr. 1, 2012, 11 pages.

(56) References Cited

OTHER PUBLICATIONS

U.S. Appl. No. 12/645,019, Notice of Allowance dated Oct. 21, 2010, 10 pages.
U.S. Appl. No. 14/064,582, Final Office Action dated Dec. 31, 2015, 17 pages.
U.S. Appl. No. 14/064,582, Non-Final Office Action dated Sep. 15, 2014, 6 pages.
Extended European Search Report for European Application No. 17150651.2, dated Jul. 11, 2017, 10 pages.

* cited by examiner

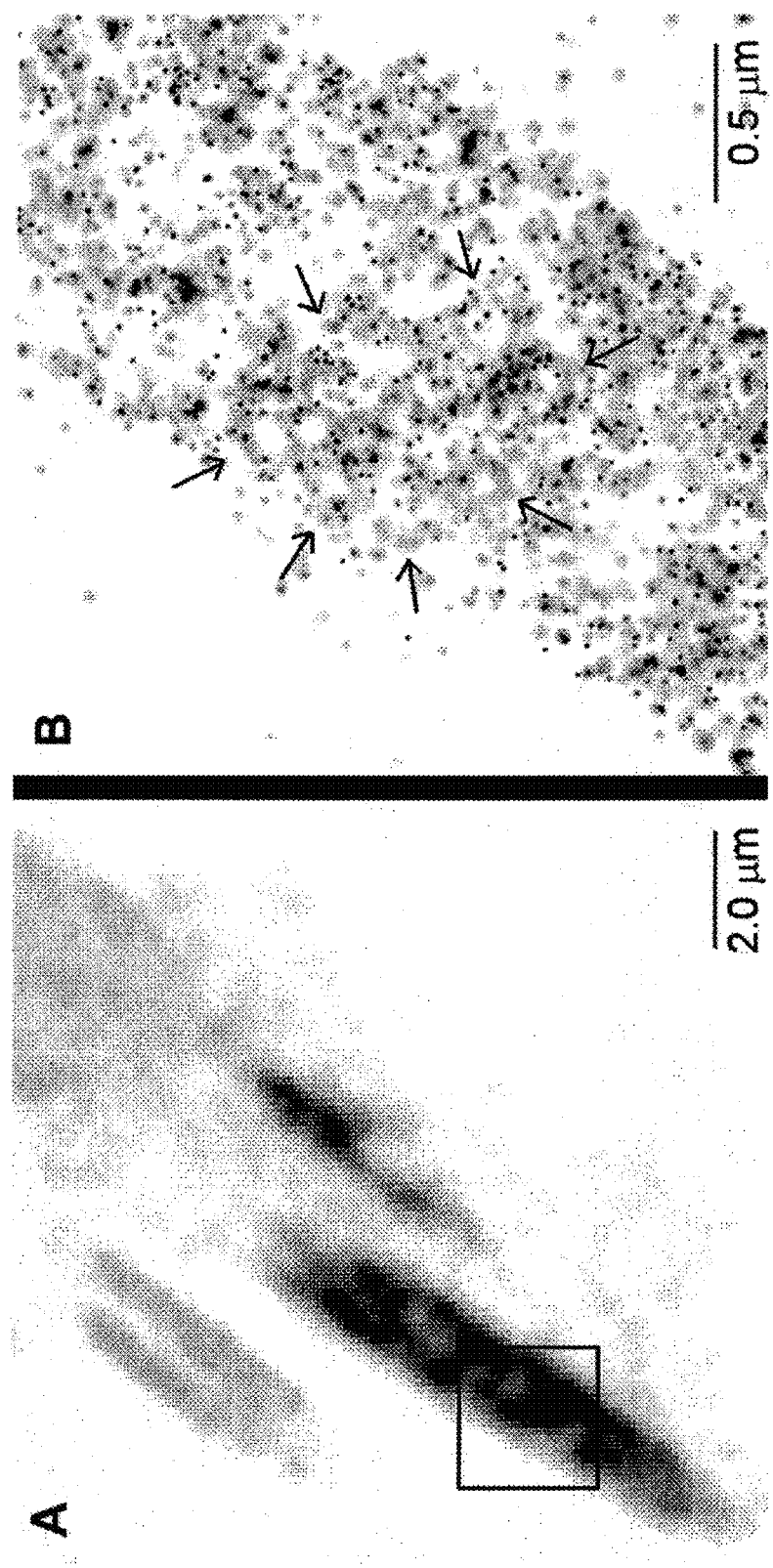

OPTICAL MICROSCOPY WITH PHOTOTRANSFORMABLE OPTICAL LABELS

CROSS-REFERENCE TO RELATED APPLICATIONS

This is a continuation application of U.S. patent application Ser. No. 14/064,582, filed Oct. 28, 2013, entitled, "OPTICAL MICROSCOPY WITH PHOTOTRANSFORMABLE OPTICAL LABELS," which, in turn, is a continuation application of U.S. patent application Ser. No. 13/655,102, filed Oct. 18, 2012, entitled, "OPTICAL MICROSCOPY WITH PHOTOTRANSFORMABLE OPTICAL LABELS," now U.S. Pat. No. 8,599,376, which, in turn, is a continuation application of U.S. patent application Ser. No. 12/956,946, filed Nov. 30, 2010, entitled, "OPTICAL MICROSCOPY WITH PHOTOTRANSFORMABLE OPTICAL LABELS," which, in turn, is a continuation application of U.S. patent application Ser. No. 12/645,019, filed Dec. 22, 2009, entitled, "OPTICAL MICROSCOPY WITH PHOTOTRANSFORMABLE OPTICAL LABELS," now U.S. Pat. No. 7,864,314, which, in turn, is a continuation application of U.S. patent application Ser. No. 11/944,274, filed Nov. 21, 2007, entitled, "OPTICAL MICROSCOPY WITH PHOTOTRANSFORMABLE OPTICAL LABELS," now U.S. Pat. No. 7,782,457, which, in turn, is a continuation application of, and claims priority to, International Patent Application No. PCT/US2006/019887, filed May 23, 2006, entitled, "OPTICAL MICROSCOPY WITH PHOTOTRANSFORMABLE OPTICAL LABELS," which, in turn, claims priority to U.S. Provisional Patent Application No. 60/683,337, filed May 23, 2005, entitled, "OPTICAL MICROSCOPY WITH PHOTOTRANSFORMABLE OPTICAL LABELS," and to U.S. Provisional Patent Application No. 60/780,968, filed Mar. 10, 2006, entitled, "IMAGING INTRACELLULAR FLUORESCENT PROTEINS AT NEAR-MOLECULAR RESOLUTION," all of which are incorporated by reference for all purposes.

BACKGROUND

A paper by one of the inventors, E. Betzig, Opt. Lett. 20, 237 (1995), which is incorporated herein by reference for all purposes, described a method to improve the m-dimensional spatial resolution in the image of a sample that includes a dense set of discrete emitters (e.g., fluorescent molecules) by first isolating each discrete emitter in an (m+n)-dimensional space defined by the m spatial dimensions and n additional independent optical properties (e.g., excitation or emission polarization or wavelength of the illumination light, fluorescence lifetime of the fluorescent molecules, etc.). After isolation, the m spatial coordinates of each emitter can be determined with an accuracy dependent upon the signal-to-noise-ratio (SNR) of the imaging apparatus, but generally much better than the original spatial resolution defined by the m-dimensional diffraction limited resolution volume ("DLRV") of the imaging optics. The map of all spatial coordinates determined in this manner for all emitters then yields a superresolution image of the sample in the m-dimensional position space.

Successful isolation of each emitter by this approach requires a mean volume per emitter in m+n space that is larger than the (m+n)-dimensional point spread function PSF. Consequently, a high molecular density of emitters (e.g. fluorescent molecules) in the sample requires high (m+n)-dimensional resolution by the imaging optics. In the 1995 paper by Betzig, it was estimated that emitting molecules having molecular density of about 1 molecule per cubic nanometer nm could be isolated with near-field microscopy/spectroscopy at cryogenic temperatures (e.g., 77 K) if the molecules were located in a matrix that introduced sufficient inhomogeneous spectral broadening. However, with conventional optical microscopy and the broad molecular spectra that exist under ambient conditions, the density of most target molecular species would be far too high for this approach to be used.

SUMMARY

In a first general aspect, a method includes providing first activation radiation to a sample that includes phototransformable optical labels ("PTOLs") to activate a first subset of the PTOLs in the sample. First excitation radiation is provided to the first subset of PTOLs in the sample to excite at least some of the activated PTOLs, and radiation emitted from activated and excited PTOLs within the first subset of PTOLs is detecting with imaging optics. The first activation radiation is controlled such that the mean volume per activated PTOLs in the first subset is greater than or approximately equal to a diffraction-limited resolution volume ("DLRV") of the imaging optics.

In another general aspect, a method of imaging with an optical system characterized by a diffraction-limited resolution volume is disclosed. In a sample including a plurality of PTOL distributed in the sample with a density greater than an inverse of the diffraction-limited resolution volume of the optical system, a first subset of the PTOLs in the sample are activated, such that the density of PTOLs in the first subset is less than the inverse of the diffraction-limited resolution volume. A portion of the PTOLs in the first subset of PTOLs is excited, and radiation emitted from the activated and excited PTOLs in the first subset of PTOLs with the imaging optics is detected. Locations of activated and excited PTOLs in the first subset of PTOLs are determined with a sub-diffraction-limited accuracy based on the detected radiation emitted from the activated and excited PTOLs.

In another general aspect, a method includes providing activation radiation to a sample that includes phototransformable optical labels PTOLs to activate a first subset of the PTOLs in the sample. Deactivation radiation, having a spatially-structured radiation field including intensity minima, is provided to the sample to transform activated PTOLs to an unactivated state, such that a second subset of PTOLs located substantially at the minima of the resetting radiation remain activated, while activated PTOLs exposed to the resetting radiation outside the minima are substantially transformed in an unactivated form. Excitation radiation is provided to the sample to excite at least a portion of the activated PTOLs in the sample, and radiation emitted from the activated and excited PTOLs is detected with imaging optics. The intensity of the first activation radiation is controlled and at least one of the intensity and the spatial structure of the deactivation radiation is controlled such that the mean volume per activated PTOL in the first subset is greater than or approximately equal to DLRV of the imaging optics.

In another general aspect, an apparatus includes a position-sensitive detector adapted for detecting intensities of radiation as a function of position on the detector, an optical system characterized by a diffraction-limited resolution volume and adapted for imaging light emitted from a plurality of activated and excited phototransformable optical labels ("PTOLs") in a sample onto the position sensitive-detector. The PTOLs are distributed in the sample with a density greater than an inverse of the diffraction-limited resolution volume of the optical system. The apparatus also includes a first light source adapted for providing first activation radiation to the sample to activate a first subset of the PTOLs in the sample, a second light source adapted for providing first excitation radiation to the sample to excite a portion of the PTOLs in the first subset of the PTOLs, and a controller adapted for controlling the activation radiation provided to the sample such that a density of PTOLs in the first subset of activated PTOLs is less than the inverse of the diffraction-limited resolution volume.

BRIEF DESCRIPTION OF DRAWINGS

FIG. 12A is a conventional total internal reflection image of points of adhesion of a whole fixed cell to a substrate, made visible by fluorescence from a PTOL-tagged version of the attachment protein vinculin. FIG. 12B is a superresolution image of the same region of the whole fixed cell, obtained by isolation and precise localization of individual PTOLs.

DETAILED DESCRIPTION

Figure 1:
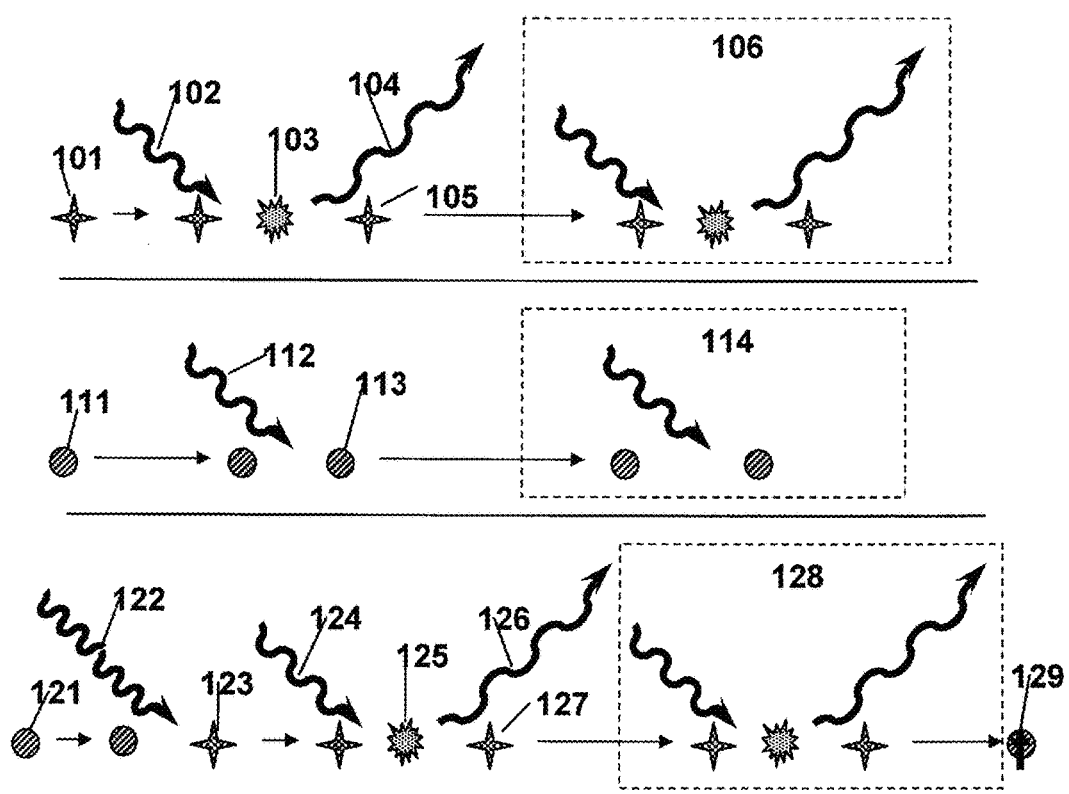
FIG. 1 is a schematic diagram of interactions between light and fluorescent dyes and between light and PTOLs.

1. Overview a. Superresolution Via Isolation and Localization of Transformable Labels

The advent of photoactivated or photoswitched optical labels, such as, for example, photoactivated or photoswitched fluorescent proteins ("FPs"), provides a variable control parameter (colloquially, a "knob") with which to control the density of activated molecules that contribute to the signal that is detected in the imaging apparatus and that is used to generate an image of the sample that contains the FPs by this process of molecular isolation and localization. Thus, the density of the FPs that contribute to the signal can be tailored to the PSF of the imaging optics to provide an image at the necessary low molecular density at any given time.

More generally, a sample can include many optical labels transformable from an inactive state (wherein the labels do not produce significant detectable radiation when excited) to an activated state (wherein the labels can emit radiation when excited) by virtue of the interaction of the transformable labels with their environment. With sufficient control over at least one activating environmental parameter, a controllable, sparse subset of the labels can be activated. These activated labels can then be excited into excited states, from which they can emit fluorescence radiation that can be imaged by an optical system. By controlling the activation environment and exciting radiation, the mean volume per activated and excited label that emits radiation can be greater than the DLRV characteristic of the optical system. By detecting radiation from such a sparse subset of emitting labels, the location of the activated and excited PTOLs can be determined with superresolution accuracy. Then, the activated labels can be deactivated, and another subset of transformable labels, statistically likely to be located at different positions within the sample, can be activated by controlling at least one activating environmental parameter, and fluorescence from the second subset of activated labels can be imaged, and their locations can be determined with superresolution accuracy. This process can be repeated to determine the location of more transformable labels within the sample with superresolution accuracy. The determined locations of all the transformable labels from the different images can be combined to build up a superresolution image of the sample.

In the specific case of the photoactivatable or photoswitchable fluorescent proteins, the labels are transformed with light, and therefore these labels represent one class of phototransformable optical label ("PTOL"). The activating environmental parameter is then an activation radiation at an activation wavelength that can transform the labels to an activated state, and at least one of the intensity or the duration of the activation radiation can be controlled to activate only a sparse subset of these PTOLs within the sample. However, other forms of energy other than electromagnetic or other environmental parameters might be used to achieve controllable activation of other types of transformable labels.

b. Enhanced Resolution Via Overlapped Spatially Structured Activation and Excitation In another example, a sample can include many PTOLs, and a subset of PTOLs located at controlled locations can be activated when the sample is illuminated with spatially-structured activation radiation. The activated PTOLs then can be excited with spatially-structured exciting radiation. The overlap of the structure of the activation radiation with the structure of the exciting radiation is controlled, such that at least one overlap region of fluorescing PTOLs comparable to or smaller than the DLRV can be produced. Fluorescence from the subset of the activated and excited PTOLs then can be detected and recorded. The activated PTOLs then can be deactivated, and a second subset of PTOLs can be activated with spatially-structured activation radiation and excited with spatially-structured excitation radiation, to generate at least one overlap region of fluorescing PTOLs in a second subset at a different location than the first overlap region, and fluorescence from the second overlap region can detected and recorded. This process can be repeated at multiple locations in the sample to build up a superresolution image of the sample.

c. Superresolution Via Spatially Structured Partial Deactivation

In a further example, a sample can include many PTOLs, and the PTOLs can be activated with spatially-structured activation radiation. A spatially-structured deactivation radiation field having one or more nodes can then be applied to the activated PTOLs, with nodes of the deactivation radiation overlapping one or more regions of activated PTOLs. The deactivation radiation is controlled so that substantially all the activated PTOLs are deactivated, except for those activated PTOLs near each node. Thus, the remaining activated PTOLs are confined to one or more regions substantially smaller than the DLRV. The activated PTOLs that remain after the application of the deactivation radiation lattice can be excited by an exciting radiation field, and fluorescence from the excited PTOLs can be detected and recorded. The remaining activated PTOLs are then deactivated with another deactivating field. This process can be repeated to build up a superresolution image of the sample.

d. Properties of Phototransformable Optical Labels

FIG. 1 is a schematic diagram illustrating how light interacts with fluorescent dyes and with PTOLs. A fluorescent molecule 101 can be stimulated by excitation radiation 102 from a ground state into an excited state 103 that emits a portion of the energy of the excited state into a fluorescence radiation photon 104. A wavelength of the excitation radiation can correspond to the energy difference between the ground state and the excited state. The molecule 101 then reverts to the ground state 105. This cycle of excitation of the molecule 101 by radiation 102 and emission of fluorescence radiation 104 can be repeated many times 106, and the fluorescence radiation can be accumulated by a microscope camera or detector. If there are many such fluorescent molecules 101 within a diffraction limited resolution volume ("DLRV") it might seem difficult to distinguish the fluorescence radiation of one molecule from another molecule.

In the case of a phototransformable optical label ("PTOL") molecule or emitter 111, the ability of the PTOL to absorb excitation radiation and therefore to emit fluorescence radiation can be explicitly turned on by an activating signal, and in certain cases, can be turned off by a deactivating signal. In an inactivated state, a PTOL 111 can be exposed to excitation radiation 112 having a characteristic wavelength, but it will radiate little, if any, fluorescence radiation at a wavelength characteristic of an activated and excited PTOL. However, when the PTOL 121 is irradiated with activation radiation 122, the PTOL 121 can be transformed into an excitable state 123. The activation radiation 122 often has a different wavelength than the wavelength of the excitation radiation, but for some PTOLs activation radiation and excitation radiation have the same wavelength and are distinguished by their intensities. After a PTOL is transformed into an excitable state 123, subsequent illumination of the activated PTOL 123 by excitation radiation 124, which generally has a different wavelength than the wavelength of the activation radiation 122, generally results in detectable emission of fluorescence radiation 126 that has a different wavelength than the wavelength of the excitation radiation 124. This process of excitation and emission can be repeated numerous times 128 for an activated PTOL 127 until the PTOL eventually bleaches or deactivates, at which point the PTOL 129 can no longer be excited and can no longer emit fluorescence radiation.

Thus, a PTOL 121 can be illuminated with activation radiation 122 having an activation wavelength, thereby transforming the PTOL into an activated state 123. The activated PTOL 123 can be illuminated with excitation radiation 124 having an excitation wavelength that is generally different from the wavelength of the activation radiation 122 to excite the PTOL into an excited state 125, from which the PTOL 125 can emit radiation 126 at an emission wavelength that is generally longer that the wavelength of the excitation wavelength 124. For some species of PTOL, the PTOL can be transformed from an activated state 123 back to an unactivated state 121, either through spontaneous decay to the unactivated state or through the application of de-activation radiation.

Several photoactivatable fluorescent proteins useful for superresolution microscopy are described below. An FP is a particular kind of phototransformable optical label ("PTOL") or substance whose optical properties can be altered by light and that can be used to label a portion of a sample to image optically the portion of the sample. As used herein "fluorescence" and "fluorescent" generally designate an optical response of the PTOL. In addition to the common understanding of fluorescence (e.g., emission of a photon from a substance in response to excitation by a more energetic photon) we include other properties that can characterize the PTOL. For example, we include emission of a photon in response to multi-photon excitation, or a large elastic optical cross section that can be activated or deactivated.

One type of PTOL is a variant of the Aequorea victoria photoactivated green fluorescent protein ("PA-GFP")—a variant of a protein derived from the Aequorea genus of jellyfish by genetic modification, as described in G. H. Patterson and J. Lippincott-Schwartz, Science 297, 1873 (2002), which is incorporated herein by reference, for all purposes. This variant can include a isoleucine mutation at the 203 position (T203) (e.g., a histidine substitution at the 203 position) of wild-type GFP and results in a molecule that has a primary absorption peak in its unactivated state at about 400 nm and a secondary emission peak with an absorption peak that is about 100× weaker centered around about 490 nm. Radiation is emitted from the excited GFP in a spectrum that centered approximately around a wavelength of about 509 nm. After intense illumination of the PA-GFP with radiation having a wavelength of about 400 nm, the 400 nm absorption peak decreases by about 3×, while the about 490 nm absorption peak increases by about 100×. Therefore, excitation of the PA-GFP with 490 nm excitation radiation to create fluorescence radiation will predominantly show only those PA-GFP molecules that have been locally activated with prior irradiation with intense 400 nm light. Other forms of photoactivatable GFP can also be used.

Photoswitchable cyan fluorescent protein ("PS-CFP"), as described in D. M. Chudakov, et al., Nature Biotechnol. 22, 1435 (2004), which is incorporated herein by reference for all purposes, has properties that are similar to those of PA-GFP, except that for PS-CFP, weak illumination with radiation having a wavelength of about 400 nm can yield fairly bright emission at about 470 nm when the PS-CFP is in its unactivated state, which allows initial set-up and targeting to be readily performed. Intense excitation of the PS-CFP at the same wavelength, about 400 nm, causes photoswitching of the protein to a version having a peak in the absorption spectrum of excitation radiation at about 490 nm and an emission peak at about 511 nm. Therefore, imaging PS-CFP labels within a sample by exciting the sample with about 490 nm excitation radiation and detecting the about 510 nm fluorescence radiation will predominantly image only those PS-CFP molecules that have been activated with prior about 400 nm excitation. PS-CFP emission is somewhat weaker than that for PA-GFP, due to its lower quantum yield, although fluorescence emission at about 510 nm increases by about 300× after activation with the approximately 400 nm radiation, as compared with an increase of about 100× at the emission peak for PA-GFP.

Kaede, as described in R. Ando, H. Hama, M. Yamamoto-Hino, H. Mizuno, and A. Miyawaki, Proc. Natl. Acad. Sci. USA 99, 12651 (2002), which is incorporated herein by references for all purposes is like PS-GFP, in that Kaede shifts its emission band upon activation. However, unlike PS-GFP, activation occurs at a different wavelength (350-400 nm) than the peak absorption wavelength in the unactivated state (508 nm), so that the unactivated protein can be observed at length without causing photoconversion to the activated state. The fluorescence emission spectrum in the unactivated state peaks at about 518 nm, while in the activated state the absorption spectrum (of excitation radiation) and emission spectrum (of fluorescence emission) peak at about 572 nm and about 582 nm, respectively. Hence, with Kaede, excitation at either the activated or unactivated peak may cause unintended excitation of molecules in the opposite state. An even brighter protein with an even greater spread in unactivated/activated emission peaks is commercially available as Kikume Red-Green, and a monomeric type, PA-mRFP1 also has been developed, as described in V. Verkhusha and A. Sorkin, Chemistry and Biology 12, 279 (2005), which is incorporated herein by reference for all purposes. The long wavelength excitation/emission in the activated state of these proteins may help reduce background for single molecule detection.

Kindling fluorescent proteins ("KFP"), which are described in D. M. Chudakov, et al., Nature Biotechnol. 21, 191 (2003), which is incorporated herein by reference for all purposes have several distinguishing characteristics relative to the others FPs described above. First, for KFPs, activation occurs at longer wavelengths (525-570 nm), which can inflict less damage on a sample and which can be easier to generate. Second, activation under low intensity illumination naturally reverses with a half-life of about 50 seconds. Third, activation under low intensity is reversible under illumination with blue light. Fourth, activation under high intensity at 525-570 nm is irreversible, even under illumination in blue light. Thus, molecules not only can be "turned-on", but "turned-off" as well, or set permanently "on". However, KFP1 currently has a relatively low quantum yield and is tetrameric.

Dronpa is a bright, monomeric fluorescent protein, described in R. Ando, H. Mizuno, and A. Miyawaki, Science 306, 1370 (2004), which is incorporated herein by references for all purposes that can be activated/deactivated over many cycles. Activation of Dronpa occurs at about 400 nm, with the activated molecules having an about 490 nm absorption peak, and an about 510 nm emission peak. The molecules revert to the unactivated state under continued exposure to the about 490 nm excitation. This cycle of activation/deactivation can be repeated at least about 100 times, with only a relatively low loss in total fluorescence during such cycling. However, during such cycling observation of the activated molecules can lead to their deactivation, possibly before the deactivation of the molecules is desired.

Given the diversity of PTOL species with different activation, excitation, and emission wavelengths and time constants, it is possible to construct separate images for each species of PTOLs. Thus, different components of a sample can be tagged with distinct labels, and each labeled object can then be independently identified in a super-resolution image that can be constructed as disclosed herein.

It is possible to label specific sample features of interest with PTOLs, such that the PTOLs, and therefore the specific sample features, can be imaged. For PTOLs that can be genetically expressed (e.g., the photoactivable fluorescent proteins), DNA plasmids can be created and inserted into the cell by transient transfection, so that fluorescent protein PTOLs are produced fused to specific proteins of interest. Likewise, stable transfections that permanently alter the genetic makeup of a cell line can be created, so that such cells produce fluorescent protein PTOLs. PTOLs also can be tagged to specific cellular features using immunolabeling techniques, or high-specificity small molecule receptor-ligand binding systems, such as biotin ligase.

Figure 2:
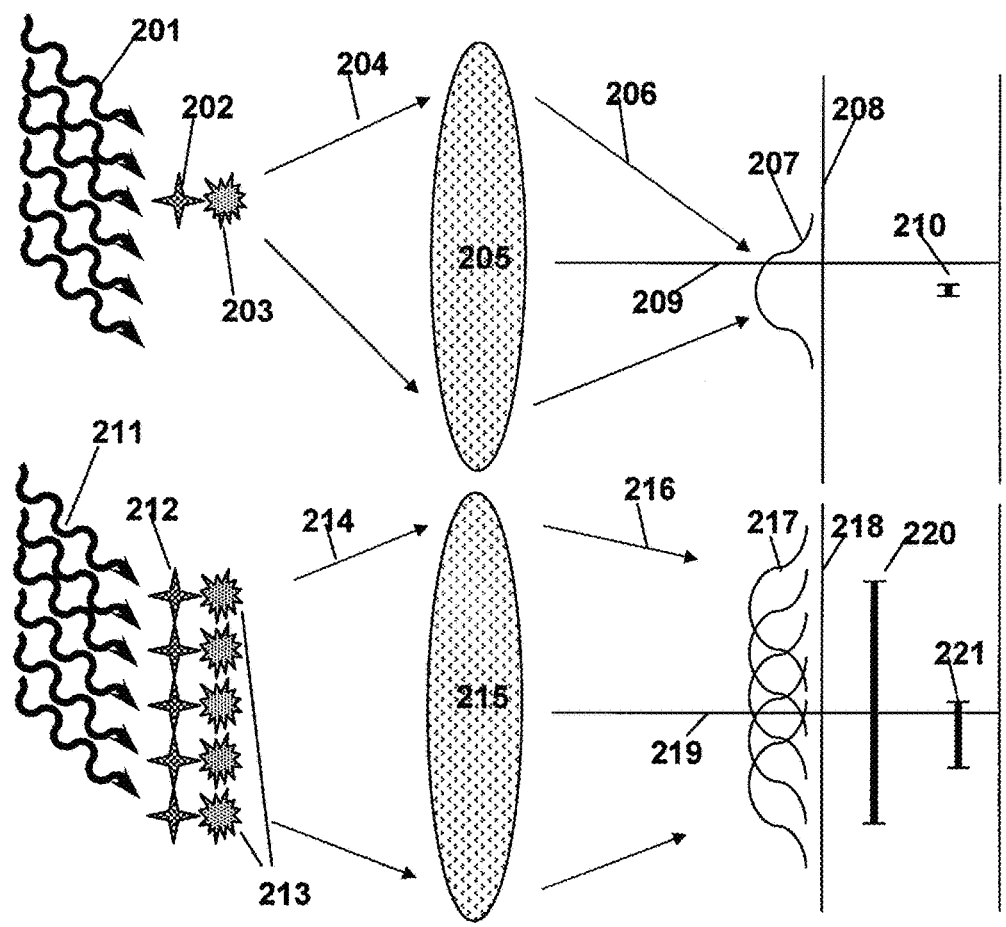
FIG. 2 is a schematic diagram of an optical imaging system, e.g., a microscope, that illustrates how a single fluorescent emitter or multiple ones can create diffraction limited images.

2. Superresolution Via Isolation and Localization of Phototransformable Optical Labels a. General Concepts Radiation from molecules or emitters can be used for sub-diffractive localization of PTOLs when the radiating molecules or emitters are isolated and spaced further apart from each other than the diffraction limited length scale of the imaging optics. For example, as shown in FIG. 2, excitation radiation 201 can excite an isolated emitter 202 into an excited state 203. Outgoing radiation 204 emitted from the excited emitter 203 can be collected by microscope optics 205 and refocused 206 onto a diffraction limited spot 207. This spot profile is shown plotted on the axis of position 208 versus emission intensity 209 in the image plane 208. The image and object plane are scaled by the magnification M. In the image plane 208, the minimum spatial width of this spot is characterized by fundamental limitation of resolution of microscopes and is given by the Abbe criteria $\Delta x \approx 0.5 * \lambda * M/NA$, where $\lambda$ is the wavelength of emission radiation 204 and NA is the numerical aperture of the objective 205. One can use this magnified image of the isolated emitter to localize the emitter to sub-diffractive precision by measuring the distribution of the emission at a detector such as a CCD camera. This data can then be fit or otherwise processed to find the center of the detected signal. For example, the emission intensity profile of light emitted from a PTOL and detected on a detector can be characterized by the discrete data set, $\{n_i\}$, where $n_i$ are the number of photons detected in the $i^{th}$ pixel of the detector located at position $x_i$. This data can be fit to a peaked function to determine a location of the PTOL. For example, a Gaussian function, $$n_i = \frac{N}{\sqrt{2\pi}\,\sigma} e^{-\frac{(x_i - x_c)^2}{2\sigma^2}},$$

can be used to perform the fit. A least squares fit of the data to the peaked function, for example, can find a value for the peak center location $x_c$. In addition other parameters, such as, for example, the total number of photons detected, N, and the peak width, $\sigma$, (which can be generally on the order of $\Delta x$) can also be deduced from the fit. Errors in $n_i$ can be expressed by a value, $\delta n_i$, and likewise the uncertainty in the center position, $x_c$, can be expressed as through a parameter, $\delta x$. In particular, when the system noise is limited by photon shot noise statistics (meaning $\delta n_i = \text{sqrt}(n_i)$) arising from the detected signal and N is the number of photons detected, then the accuracy to which this center can be localized is given by $\delta x = \Delta x/\text{sqrt}(N)$. To the extent that N is much larger than unity, the localization accuracy 210 can be significantly better than the diffraction limit 221. The data also can be fit to other functions than the Gaussian function to determine a center location and width of the position of a PTOL.

However, it can be difficult to apply this technique to a set of continuously-emitting fluorescent molecules 212 that are spaced so closely together that they are within $\Delta x$ of each other. In this case, the diffractive spots are highly overlapped, such that fitting of the image of a molecule to obtain a position of the molecule with superresolution accuracy is difficult. Thus, in this situation the resolution limit generally is given by standard Abbe criterion 221, i.e. the width of the diffractive limited spot.

Figure 3:
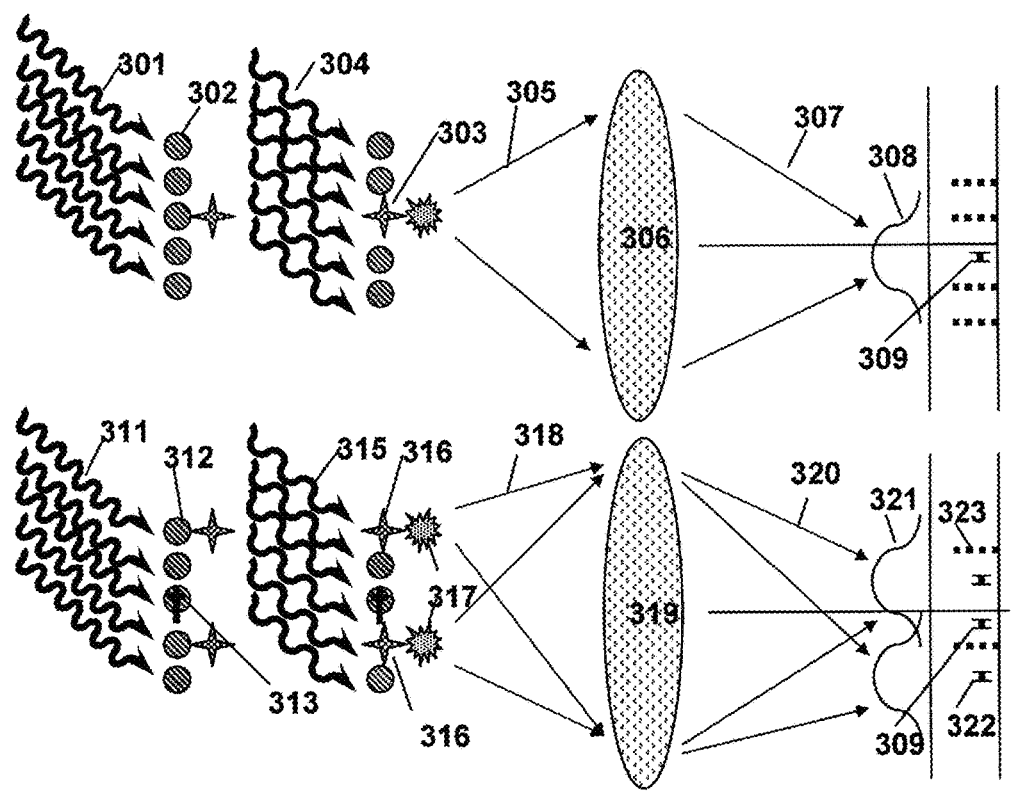
FIG. 3 is a schematic diagram illustrating how a sparse subset of activated PTOLs can be imaged and localized to sub-diffractive accuracy in one spatial dimension without interfering emission from neighboring PTOLs. The lower half of FIG. 3 illustrates how a second or subsequent activation can image a sparse subset of remaining PTOLs which in-turn can also be localized to better than diffraction-limited accuracy. Repeated application of this procedure can resolve many individual PTOLs that are otherwise too close to resolve by conventional fluorescence.

However, by selectively activating and de-activating subsets of PTOLs within a dense set of PTOLs this localization concept can be used even when the optical labels are closely spaced. As shown in FIG. 3, weak intensity activation radiation 301 can bathe closely spaced PTOLs 302. A small, statistically-sampled fraction 303 of all the PTOLs absorbs the activation radiation and is converted into a state 303 that can be excited by the excitation radiation 304. The emission radiation 305, 307 from this activated and excited subset is focused to a set of isolated, diffraction limited spots 308 whose centers can be localized to sub-diffractive resolution 309 as illustrated previously in FIG. 2. After enough photons are collected to generate sufficiently resolved images of the PTOLs that are members of the activated and excited subset, the activated PTOLs are either deactivated to return to an activatable state 302 (as in the case of Dronpa or KFP) or are permanently photobleached to a dark form 313, effectively removing them from the system. Another cycle of weak intensity activation radiation 311 is then applied to activate a new subset 316 of the remaining activatable PTOLs 312. The PTOLs in this second subset in turn can be put into the excited state 317 by excitation 315. The radiated light 318, 320 is refocused by the microscope lens 319 onto well-separated diffractive resolution limited spots 321. Once again, fitting of each peak can define the sub-diffractive locations 322 of the PTOLs in the second subset. Further cycles will extract sub-diffractive locations of other PTOLs, such as PTOL image locations 323.

Figure 4:
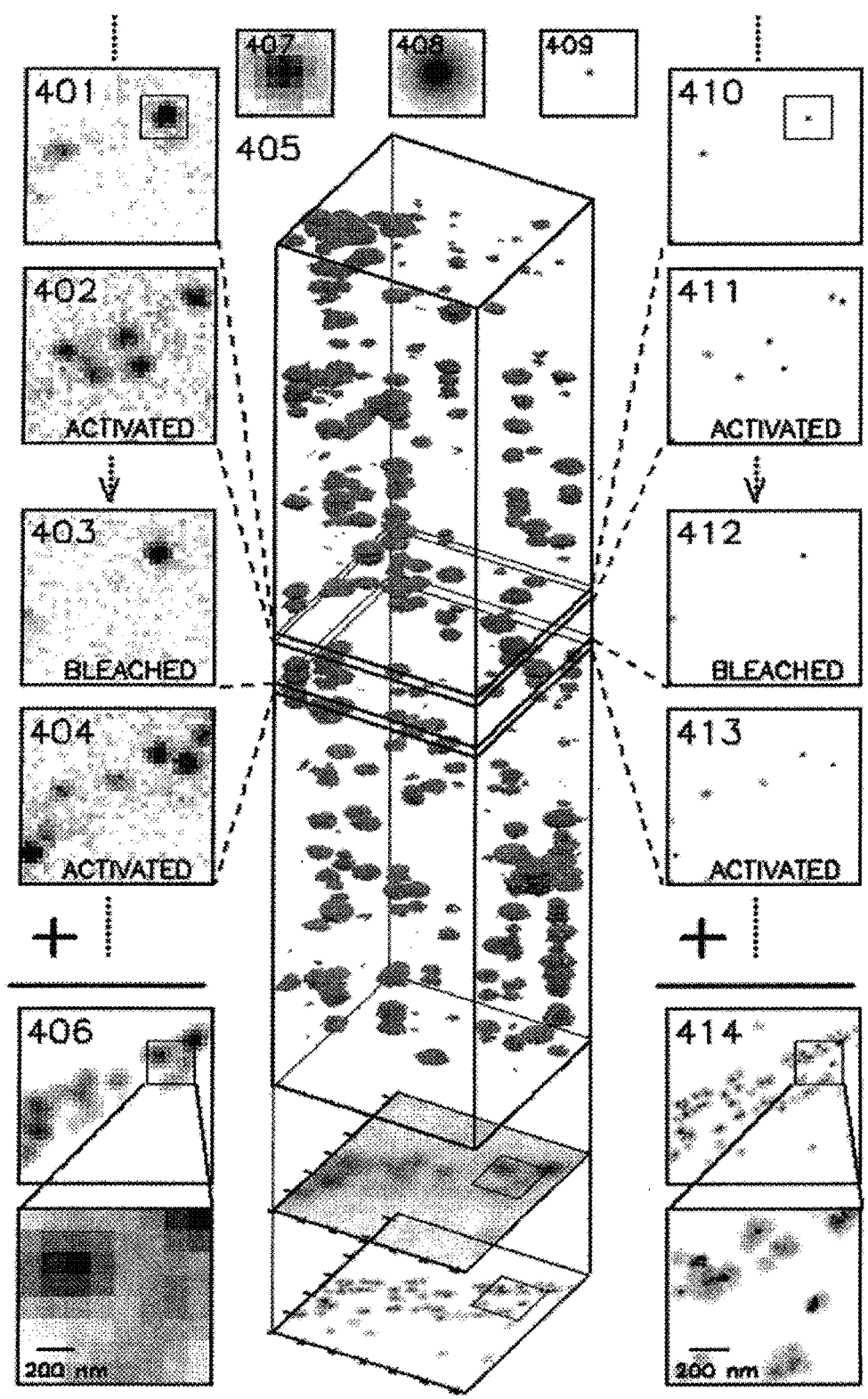
FIG. 4 is a schematic diagram illustrating how a sparse subset of activated PTOLs can be imaged and localized to sub-diffractive accuracy in two spatial dimensions without interfering emission from neighboring PTOLs. The images of sparse diffraction-limited spots are on the left side of FIG. 4, and the localized centers of the spots are rendered as corresponding images on the rights side of FIG. 4. An accumulation of such images on the right gives the super resolution images of the lower right corner.

As shown in FIG. 4, multiple sub-diffractive resolution images in two spatial dimensions, x and y, of individual PTOLs in a sample can be generated, and then the multiple images can be combined to generate a sub-diffraction limited resolution image of the sample. Images shown in FIG. 4 were generated from experimental data taken with a system as described herein. An initial image of a few discrete PTOLs emitting at a wavelength that is imaged by imaging optics is shown in frame 401. After a subset of PTOLs is activated with an activation pulse of radiation having an activation wavelength different from the wavelength of radiation that is imaged, more PTOLs are detected, as shown in frame 402. Several such frames are recorded until many of these initially-activated PTOLs bleach and can no longer emit, as shown in frame 403. At this point, a new activation pulse can convert a new subset of PTOLs into an activated state, and this new subset of PTOLs can emit radiation at the imaging wavelength when the newly-activated PTOLs are excited, which results in the image of frame 404. This cycle can be repeated to generate several hundred or thousands of such image frames, which can be considered to represent a 3D data stack 405 of PTOL images, with the coordinates, x and y, on the horizontal plane and the time, t, on the vertical axis. Then all these individual image frames in the data stack can be summed to generate a total image that is equivalent to a long time exposure of a diffraction-limited image from a microscope, as shown in frame 406.

However, if activated PTOLs are sufficiently sparse in the sample, the raw signal from each activated PTOL (e.g., the intensity of the signal on individual pixels of a CCD detector), as shown in frame 407, can be fitted with an approximate point spread function (e.g., a Gaussian) to generate a smoothed, fitted signal, as shown in frame 408, and the center x,y coordinates of each PTOL can be determined. The location of each PTOL can then be rendered in a new image as a Gaussian centered at the measured localization position, having a width defined by the uncertainty to which this location is known. This uncertainty can be significantly less than the original radius of the original, diffraction-limited PTOL image 407 (typically by an approximate factor of sqrt(N), where N is the number of photons detected to generated the image of the PTOL). For example, if there were 400 photons in the pixels of the image spot of a PTOL, the uncertainty of the fitted central location can be 1/20 of the size of the original diffraction limited image of that PTOL.

Applying this process to images of all the activated PTOLs in frames 401, 402, 403, and 404 leads to the corresponding narrow rendered peaks in frames 410, 411, 412, and 413. The widths of these rendered peaks are given by their localization uncertainty. Applied to all activated PTOLs in all frames of the data stack 405, this localization process results in a list of coordinates for many PTOLs within the sample. Alternatively, the rendered peaks can be accumulated (e.g., summed) to give a superresolution image 414 of a dense set of PTOLs. The emission of any activated PTOL may persist over several frames until it is bleached or otherwise deactivated. For such a case, an implementation of this accumulation is to identify the coordinates across several frames of what is likely to be a common PTOL. This set of coordinates can be averaged or otherwise reduced to obtain a single, more accurately localized coordinate vector of that PTOL. A comparison of the diffraction limited image 406 and the superresolution image 414 illustrates the higher resolution achievable by this process.

When the sample drifts over the course of acquiring a data stack, images of the sample can be acquired while simultaneously tracking fiducial markers (e.g., a single quantum dots) added sparsely to the sample, and correcting for the drift thereby measured during the post-acquisition analysis. Such fiducial-based drift compensation may also facilitate the adaptation of the techniques described herein to commercial microscopes, allowing the investigation of samples at various magnifications and under a variety of established imaging modalities (e.g., differential interference contrast ("DIC")) in addition to using the techniques described herein. Quantum dots that are sparsely added to samples as fiducial marks to compensate for sample drift observed during data acquisition can be isolated and localized in the same manner as single PTOLs.

This process of serial activation of different isolated PTOL subsets allows an effective way of localizing the positions of a dense set of PTOLs, such that superresolution images in 1, 2, or 3 spatial dimensions can be generated, as described in more detail herein. Furthermore, this process can also be independently repeated for different species of PTOLs within a sample, which have different activation, excitation, and/or emission wavelengths. Separate or combined superresolution images can then be extracted using each PTOL species. The extracted positional information of two or more different PTOLs that label two different binding proteins can describe co-localization and relative binding positions on a common or closely connected target. This can be useful for determining which proteins are related to each other.

Figure 5:
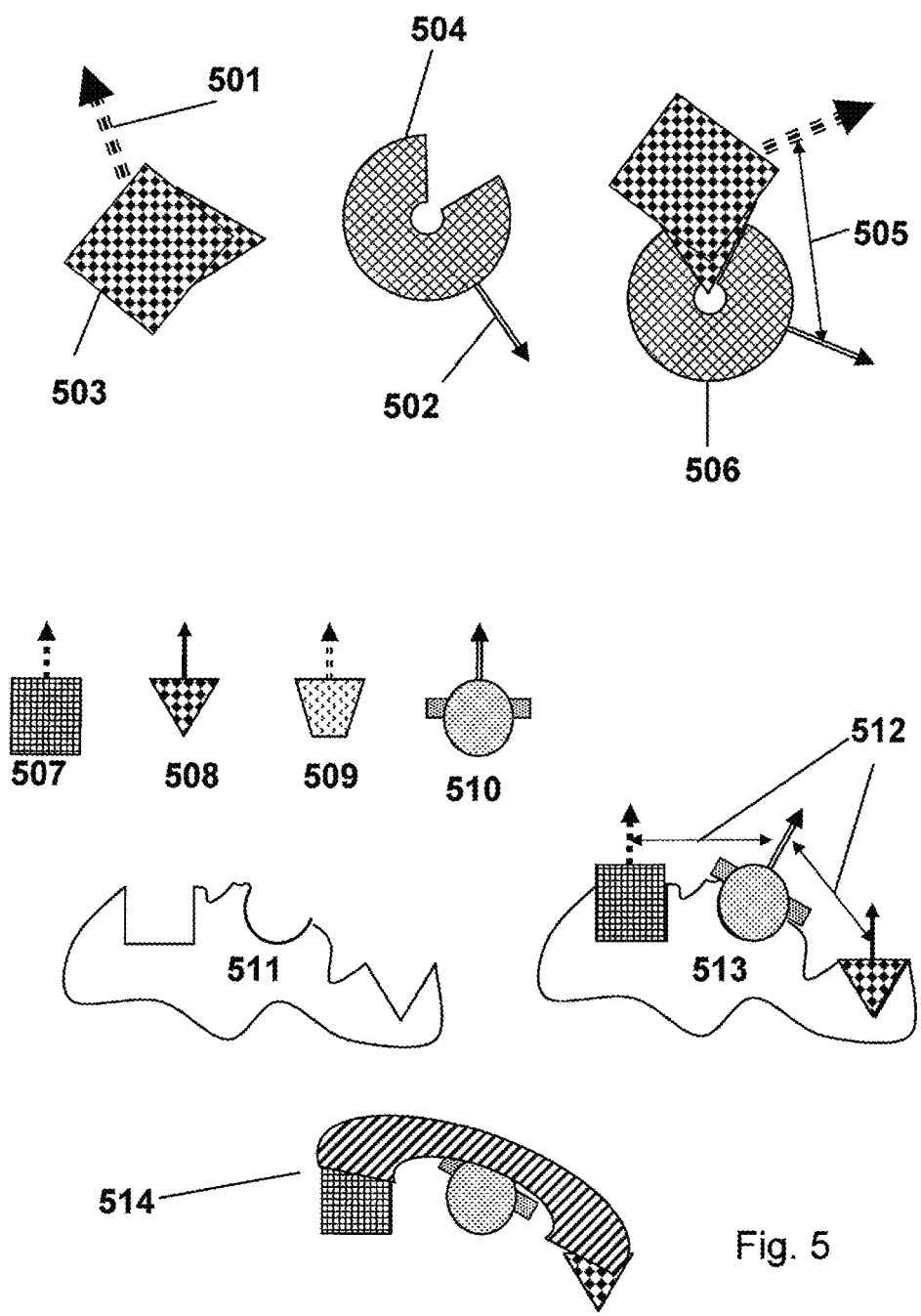
FIG. 5 is a schematic diagram illustrating how different types of proteins labeled with different PTOL species can be co-localized and how relative distances and positions within a DRLV of each of the label types can be extracted. Potential uses are in protein co-localization tests, or affinity tests or affinity mapping, e.g., for synthetic drug design.

An example of how multiple PTOL species can be used to provide molecular binding (e.g., co-localization) information and molecular structural information is illustrated in FIG. 5. For example, two different PTOL species 501 and 502 can label two different molecules proteins 503 and 504, for example, when the PTOL species 501 selectively binds to protein 503, and the PTOL species 502 selectively binds to protein 504. If these two proteins 503 and 504 bind to each other to form a molecular complex 506, then the two PTOLs 501 and 502 can be located at a short distance 505 from each other and therefore radiate in close proximity to each other. The distance 505 between such co-localized molecules (e.g., proteins 503 and 504) can be less than the size of the molecular complex 506. Because the PTOL species can be imaged, and their locations determined, independently with the methods and systems described herein, PTOLs 501 and 502 can be distinguished even when their locations are determined to be within the diffraction limit. Indeed, if the distance 505 is larger than the localization resolution of the systems described herein, then the quantitative value of the distance 505 between the PTOLs 501 and 502 can provide additional information about how and where these proteins 503 and 504 are bound to each other. Furthermore, the spatial orientation of each the PTOLs 501 and 502 can be deduced by the methods described herein (e.g., by observing the polarization of dipole radiation emitted from the PTOL), which in turn can also provide positional and orientational data on the relative attachment between proteins 503 and 504. In one implementation, radiation emitted from activated and excited PTOLs in a sample can be passed through a polarization filter to discriminate the emitted radiation on the basis of the emitted radiation's polarization. Because the polarization of emitted radiation is indicative of the dipole orientation of the PTOL from which the radiation is emitted, the polarization-sensitive signal detected at the detector provides information about the orientation of the emitting PTOL. This method can be extended to a larger multiplicity of various PTOL species 507, 508, 509, and 510. Co-localization experiments could determine which PTOL species 507, 508, 509, and 510 bind to each other or, for example, to another target 511. Relative distances 512 between PTOLs 507, 508, 509, and 510 bound to a target 513 can be derived from the localization methods described herein and can be used to map the type and position of the binding sites on the target 513.

One implementation of these principles of affinity identification and co-localization measurements is in drug discovery. In particular for synthetic drug design there is interest in mapping where and how strongly a library of smaller molecules can bind to various parts of the surface of a target. If a collection of such low affinity fragments can be identified and tethered together then as a group they will have high affinity for the target. There are several techniques utilized by companies in identifying such drug fragments out of a library. Such a structure activity relationship and proximity sensing can be identified by several techniques, for example, NMR, X-ray Crystallography, chemical ligation with mass spectroscopy, or surface plasmon resonance.

A similar approach can identify structural activity relationships using multiple PTOL labeled drug fragments and can identify and localize them with the phototransformable optical localization approaches described herein. For example, various PTOL species can label a library of different molecules (e.g., drug fragments) 507, 508, 509, and 510. The co-localization of a molecule 507, 508, 509, or 510 with a target 514 could confirm attachment of drug fragments to the target 514 and map the binding affinity of the surface of the target 514 using the methods described herein. The resulting co-localization and positional information along with any dipole information can be used to design a synthetic drug 514 that would have a high binding affinity to a target such as 511.

b. General Hardware and Software Requirements

Figure 6:
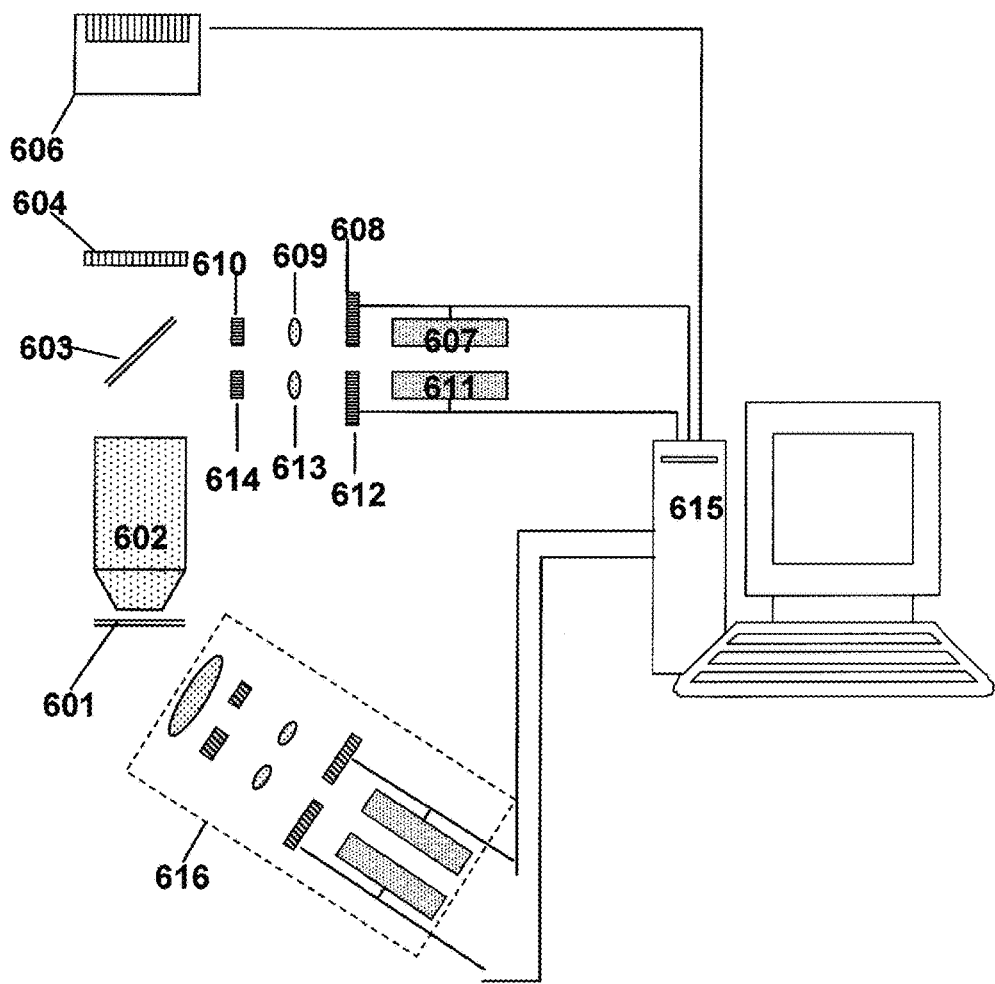
FIG. 6 is a schematic diagram of an apparatus that can localize PTOL locations to better than diffractive resolution even if their spacing is less than a DRLV. The components include the PTOL-labeled sample, an activation subsystem for the PTOLs, an excitation system for PTOLs, an imaging/detection system for the emitted light, and a control system for sequencing these tasks and acquiring the data.

FIG. 6 is a schematic view of a PTOL microscope. A sample 601 that has been labeled with PTOLs emits radiation that is collected with an imaging lens (e.g., a microscope objective lens) 602 and that can be filtered with one or more filters 604. Images of currently activated PTOLs are formed at detector 606, which in one implementation can detect single photons. Optical elements for providing activation radiation to the sample can include a light source 607, a shutter 608, a lens 609, and a filter 610. The light source 607 (e.g. one or more lasers, light emitting diodes, or broadband sources) can emit radiation at an activation wavelength that causes a PTOL to be transformed from an inactivated to an activated state. The light source 607 can be directly modulated, or modulated via the shutter 608. The shutter 608 can operate to admit or prevent activation radiation from passing from the light source 607 to the sample 601. In one implementation, the shutter can be a mechanical shutter that moves to selectively block the beam path. In another implementation, the shutter can be a material that can be modified electronically or acoustically to admit or prevent light from passing or to alter a beam path from the light source 607. The filter 610 can block certain wavelengths of radiation while passing other wavelengths. For example, if the sample 601 contains several species of PTOLs, each having different activation wavelengths, the light source may emit light at each of the activation wavelengths but various filters 610 can be inserted in the beam path between the light source 607 and the sample to block some activation wavelengths while passing other wavelengths, such that only one (or a selected few) species of PTOL is excited. Radiation from the light source 607 can be deflected by a partial reflector 603 (e.g., a beam splitter, a dichroic mirror, a spotted mirror, or a diffractive structure and directed through the imaging lens 602 onto the sample 603. Similarly, excitation radiation that causes an activated PTOL to be transformed from a de-excited state to an excited state can also be passed from an excitation light source 611, through a shutter 612, a lens 613, and a filter 614 and off a partial reflector 603 to the sample 601. A controller 615 (e.g., a general or special purpose computer or processor) can control parameters of the activation and excitation pulses (e.g., the wavelength, intensity, polarization, and duration of pulses of various radiation beams that reach the sample 601; and the timing of activation radiation pulses and excitation radiation pulses) during an image acquisition sequence. Of course, the optical elements 607-614 can be arranged in other configurations. For example, the activation optics 607-610 and/or the excitation optics 611-614 can be configured, as in the module 616, to direct radiation to the sample 601 from outside of the lens 602, or the excitation radiation can be directed onto the sample from a different partial reflector than the activation radiation, etc. Furthermore, there can be a multiplicity of components so that PTOLs of a different species can also be imaged either in parallel or in a separate sequential acquisition. For example, there can be additional cameras, filters, shutters, activation sources, or excitation sources, of different wavelengths associated with the characteristics of different PTOL species. Data from images formed at the detector 606 are communicated to the controller 615 for storage and processing. For example, the controller 615 can include a memory for recording or storing intensity data as a function of position on the detector for different image frames. The controller 615 can also include a processor for processing the data (e.g., a general or special purpose computer or processor), for example, to fit the data recorded for an image of an individual PTOL to determine a location of the PTOL to sub-diffraction limited resolution, or to combine the data about the locations of multiple PTOLs that are determined with superresolution accuracy to generate an image of the sample based on the locations of multiple PTOLs that have been located with superresolution accuracy.

Figure 7:
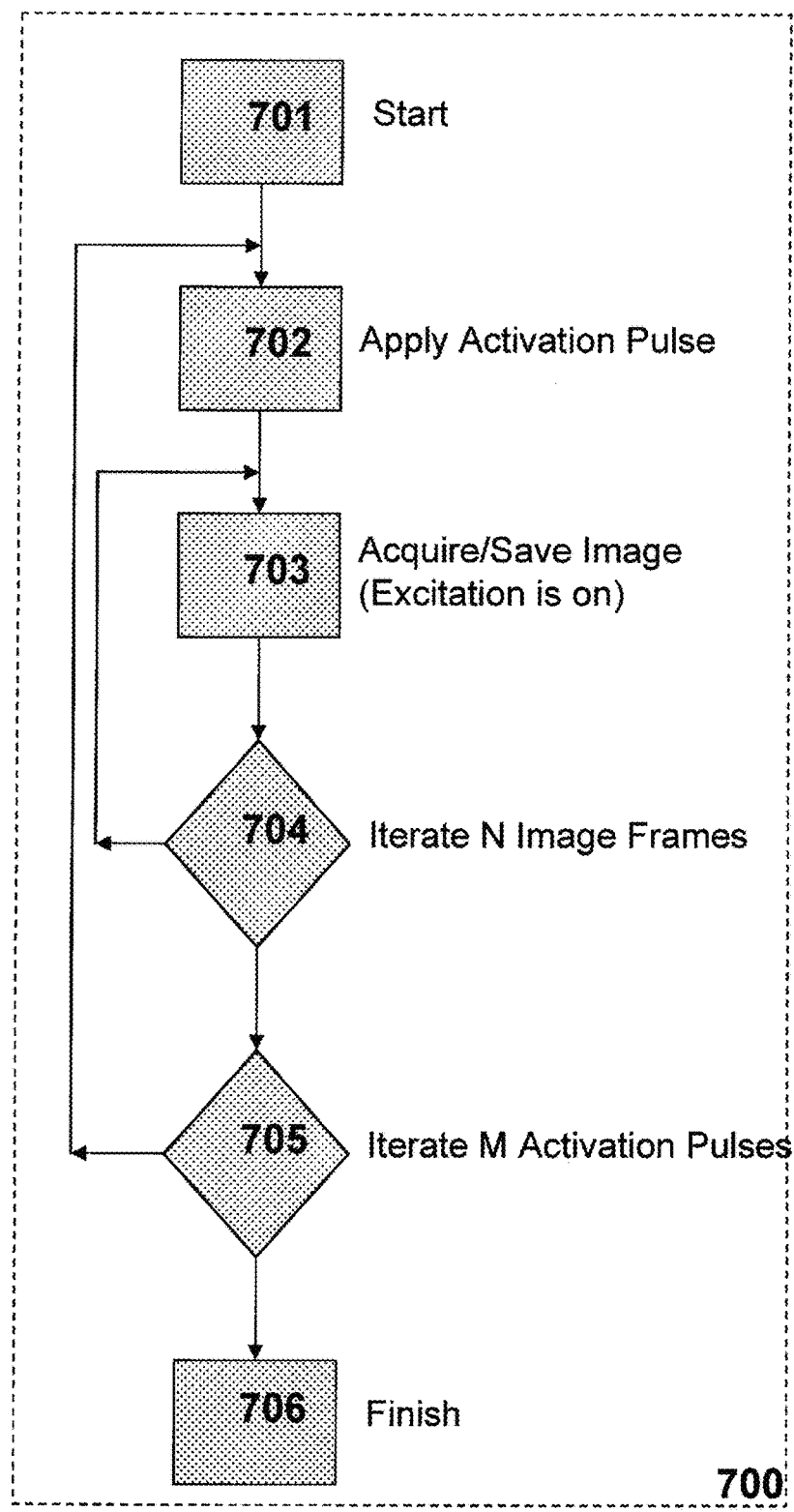
FIG. 7 is a flow chart outlining a process in which PTOLs in sample iteratively are activated, excited, and emit radiation that is detected.

FIG. 7 is a flow chart of a process 700 for creating an image of a sample containing multiple relatively densely-located PTOLs. An activation pulse of radiation having an activation wavelength is directed onto a sample to transform a subset of PTOLs in the sample from an unactivated to an activated state (step 702). Excitation radiation is applied to activated PTOLs in the sample at the excitation wavelength, and radiation that is emitted from activated and excited PTOLs and incident onto the imaging and detecting optics is acquired and saved (step 703). Images of a set of activated PTOLs can be acquired and saved multiple times. For example, the controller can require that N images of a set of activated PTOLs are acquired, such that if N images have not yet been acquired (step 704) image acquisition (step 703) is repeated. The excitation radiation can be applied to the sample continuously or can be switched off between acquisitions of images.

After N images of the subset of activated PTOLs are acquired, and if more images are to be obtained from the sample (step 705) another activation pulse can be applied to the sample to activate another set of PTOLs (step 702). Excitation radiation can be applied to this other set of activated PTOLs, and radiation emitted from the activated and excited PTOLs can be acquired and saved (step 703). Multiple sets of PTOLs can be activated. For example, the controller can require that M sets PTOLs be activated, such that if M sets have not yet been activated (step 705) another activation pulse is applied (step 703). Thus, the process of activating a set of PTOLs, exciting PTOLs within the activated set, and acquiring images from the activated and excited PTOLs can be repeated multiple times, for example, until the total pool of available PTOLs becomes exhausted or until a desired number of images of a desired number of different PTOLs within a spatial area or volume is achieved.

While applying the activation and excitation radiation, the number of iterations N between activation pulses, along with the intensity of the activation and excitation radiation can be controlled such that the mean volume per imaged PTOL in an individual image is generally more than the DLRV of the optical imaging system used to detect and localize the individual PTOLs. The density of activated PTOLs that are capable of emitting radiation is generally highest in images acquired immediately after the activation pulse and generally decreases as more PTOLs photobleach during the acquisition of the N image frames. Furthermore, as the process 700 progresses, and the number of activation pulses increases from 1 to M, PTOLs within the sample may photobleach, such that fewer and fewer PTOLs within the sample are available to be activated, excited, and imaged. Thus, in one implementation, the intensity and time length of individual activation pulses and the intensity and time length of excitation radiation can be controlled, to reduce the variation in density of activated PTOLs as the process progresses. For example, using less excitation radiation (possibly with fewer frames N between activation pulses) can reduce the decrease in imaged PTOLs from the first frame after an activation pulse to the Nth frame just preceding the next activation pulse. In another example, the intensity of individual activation pulses can increase as the process 700 progresses from the first to the $M^{th}$ activation pulse. This would reduce the decrease in the number of imaged PTOLs in the first acquisition frame after the Mth activation pulse relative to the number of imaged PTOLs in the first acquisition frame after the first activation pulse, thereby compensating for the reduction in the number of activatable PTOLs as the sequence of activation and image acquisition progresses. Thus, in the first example, the variation of activated and excitable PTOLs during an excitation sequence is reduced and in the second example the variation of activated and excitable PTOLs during the activation sequence is reduced. The reduced variation of activated and excitable PTOLs allows operation, where more PTOLs can be localized per unit time, while not exceeding the density criteria of more than one imaged PTOL per DLRV.

In one implementation, multiple species of PTOLs within the sample can be activated, excited, and imaged. For example, steps of applying the activation pulses (702) and of exciting and imaging (703) can include applying pulses of activation radiation and excitation radiation, respectively, having wavelengths corresponding to the different activation and excitation wavelengths of different PTOL species. A multiplicity of detectors and/or filters can also be used in the imaging step 703 to image different wavelengths of radiation emitted from different PTOL species. In this manner, multiple independent data sets of images can be acquired. These independent data sets in turn can be reduced to corresponding super-resolution images of each PTOL species within a sample.

c. Exemplary Excitation and Detection Geometries

The process of activating a subset of PTOLs in a sample, exciting some or all of those activated PTOLs, and imaging the activated and excited PTOLs can be applied in any optical imaging mode, for example, in widefield microscopy, total internal reflection fluorescence (TIRF) microscopy, confocal microscopy, and multifocal lattice microscopy.

As shown in FIGS. 8a, 8b, 8c, and 8d, widefield microscopy permits many individual PTOLs 800 within a sample 810 that reside near the plane of focus 801 of a lens 802 to be localized simultaneously, when the PTOLs are activated at a low enough density that their separations in the plane 801 are generally larger than the diffraction limited 2D resolution defined by the lens 802. The magnification of the imaging optics (e.g., including lens 802) is chosen relative to the size of individual pixels 803 in a detector 804 (e.g., an electron multiplying charge coupled device (EMCCD) camera) that images the PTOLs 800, so that the image 805 from each PTOL is dispersed over several pixels to optimize the localization accuracy for each PTOL. Of course, if radiation emitted from a particular PTOL were detected by only one pixel it would be difficult to determine the location of the PTOL with sub-diffraction limited accuracy, but if radiation from the PTOL falls on multiple pixels the signals from the different pixels can be fitted, such that the PTOL can be localized with sub-diffraction limited accuracy. However, if radiation from a particular PTOL falls on very many pixels, then it may overlap with the radiation from another PTOL, or the background noise from the greater number of pixels involved may be increased. In either case, such that the localization accuracy would be relatively low. Thus, a compromise between having an image of a PTOL fall on too many or too few pixels can be obtained.

Widefield microscopy is easily used with the processes described herein to achieve 2D localization of PTOLs in thin samples (i.e., samples having a thickness comparable to or smaller than the depth of focus 806 characterized by the numerical aperture of the lens and the wavelength of the fluorescence light emitted from the PTOLs). Application to such thin samples can: a) limit background signal from autofluorescence or unresolved PTOLs in areas away from the focal plane 806 (since such background can degrade the accuracy with which PTOLs are localized); b) reduce the number of potentially photoactivatable molecules within the 2D PSF; and c) when the activating energy is delivered through the imaging lens, insure that the PTOLs that are activated are generally within the focal plane of the lens, and therefore produce minimally sized spots at the detector and corresponding optimal localization.

One example of such thin sections is the lamellipodial regions of cultured cells. Another class of thin samples suitable for widefield detection is thin sections cut from a larger sample using the microtome techniques common to transmission electron microscopy (either cryosections or sections from resin-embedded cells or tissues). Such solid, cut sections insure that the PTOLs remain immobile for accurate localization, and permit deeply buried sample features to be imaged, without the problems of out-of-plane autofluorescence, aberrations, and light scattering that potentially exist when trying to image the same features by widefield microscopy in the original, thicker sample.

Figure 8A:
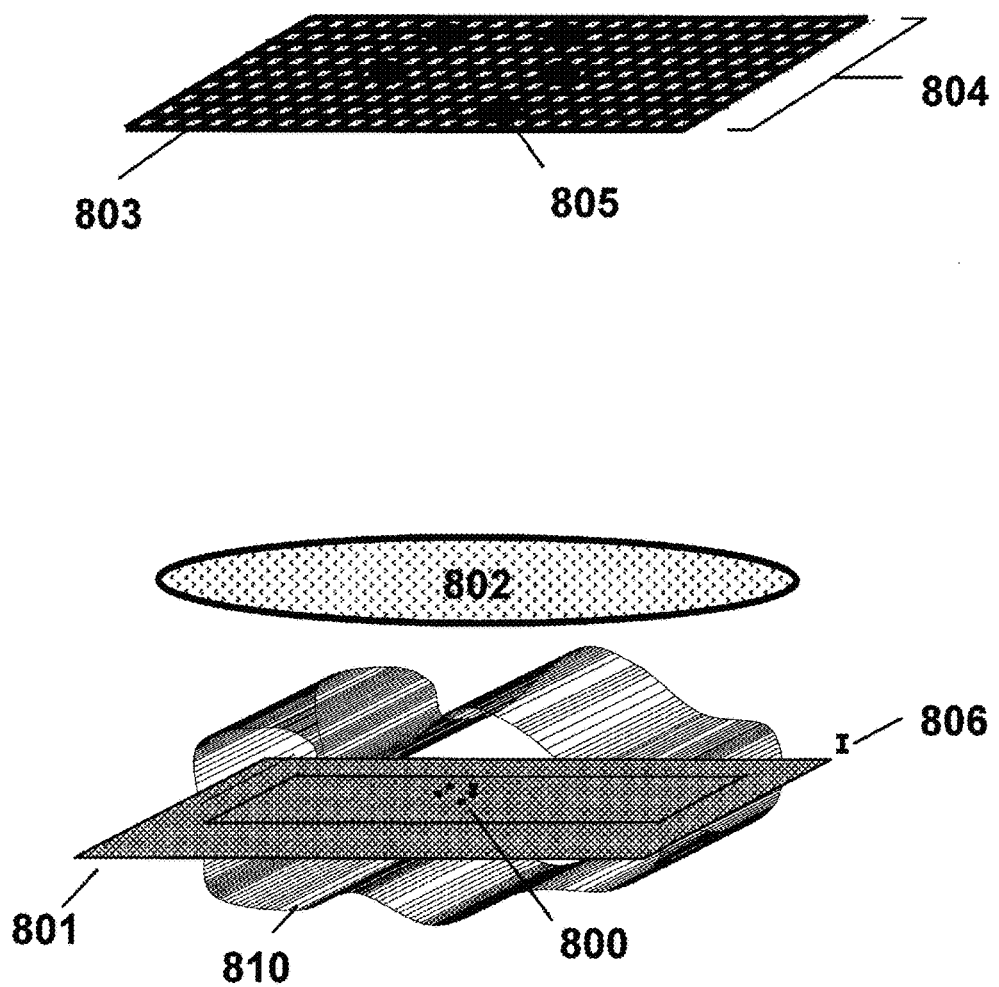
FIG. 8A is a schematic diagram illustrating the use of widefield microscopy for the detection of radiation emitted by PTOLs near the focal plane of a lens.
Figure 8B:
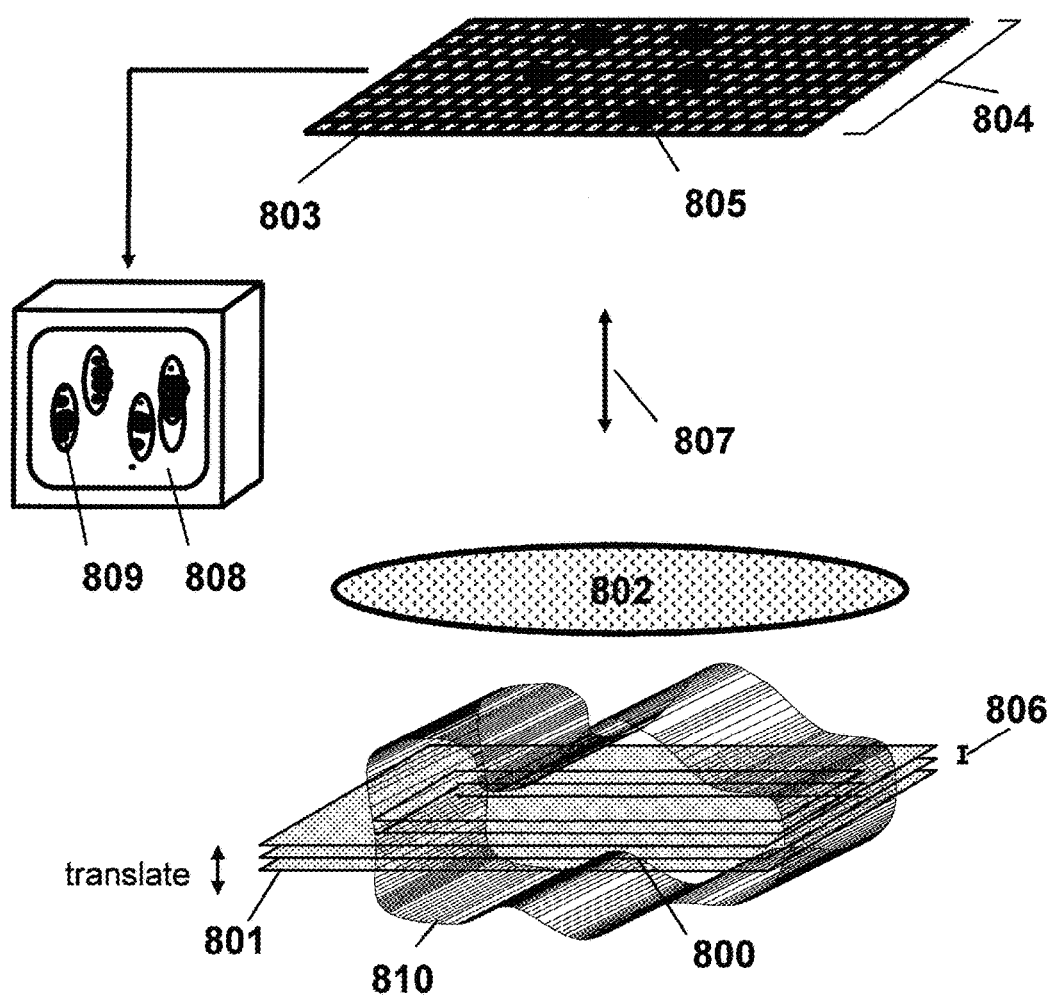
FIG. 8B is a schematic diagram illustrating the widefield detection of radiation emitted by PTOLs over a region large compared to the depth of focus of a detection lens by translating the sample relative to the lens.

As shown in FIG. 8b, in cases where widefield detection of PTOLs can be applied to samples that are thick compared to the depth of focus of the lens, localization of PTOLs in 3D can be performed by translating the focal plane along the optical axis 807 of the lens (e.g., by changing the separation between the lens and the sample) for each activated subset of PTOLs that is imaged to create 2D images of multiple planes of the sample. These multiple 2D images can be combined digitally to build an image stack 808 such that a 3D image of each imaged PTOL in the sample is obtained. Then the 3D image of each PTOL can be fitted to obtain a sub-diffraction limited position of the PTOL positions in 3D, by direct analogy to the 2D case described above. A complete 3D superresolution image can be thereby constructed from many subsets of localized PTOLs.

Another approach to providing position information for the PTOLs in the direction defined by the axis 807 of the lens is to apply the excitation light in a form that is spatially structured primarily along this direction, and substantially uniform parallel to the focal plane (so that the advantage of simultaneous detection in 2D is retained). The spatially structured field can then be scanned in the axial direction for each subset of individually resolvable, activated PTOLs, thereby permitting the axial excitation PSF to be measured at each. The known PSF of the axially structured excitation can then be fit to this data to find the relative locations of the PTOLs in the axial direction with nanometric precision. The data can then be combined with the localized coordinates of the same PTOLs in the focal plane, and further combined with similar results from other subsets of activated PTOLs to build a dense superresolution 3D image.

Figure 8C:
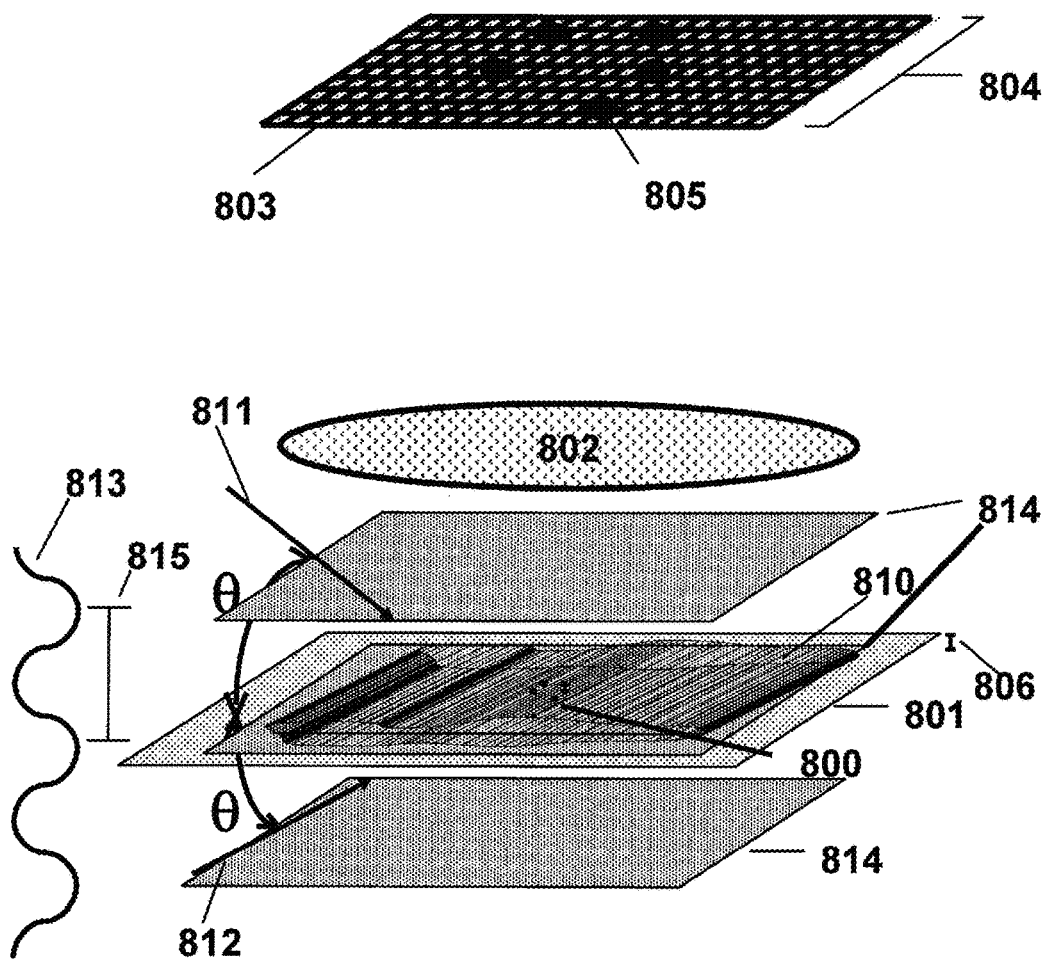
FIG. 8C is a schematic diagram illustrating the use of structured excitation in a widefield system to preferentially excite and then detect the radiation emitted from PTOLs in multiple planes.
Figure 8D:
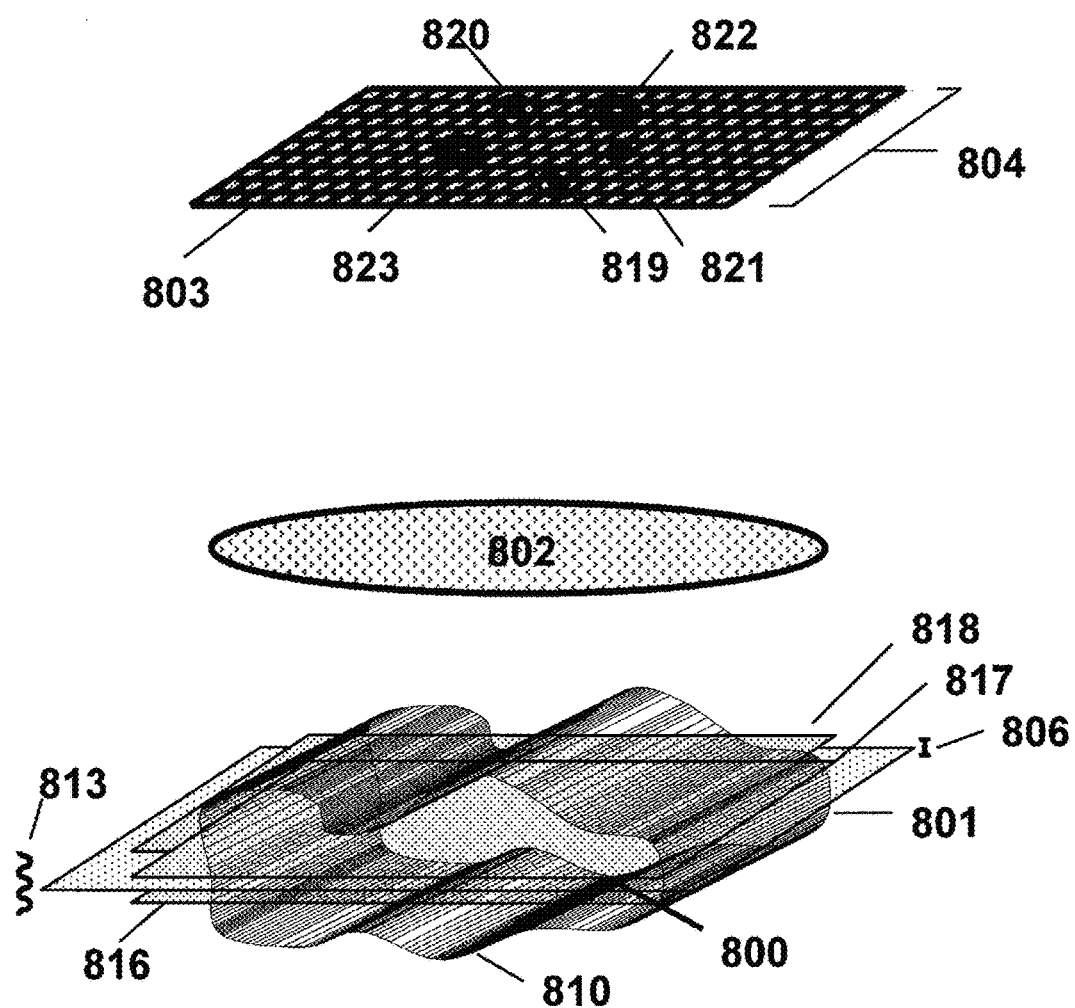
FIG. 8D is a schematic diagram illustrating the different patterns at the detector of a widefield system arising from PTOLs at different planes.

As shown in FIG. 8c, such an axially structured excitation field can be created by impinging the excitation light on the sample 810 in two coherent beams 811 and 812 from directions that are mirror imaged with respect to the detection plane. The beams 811 and 812 intersect within the sample 810 to produce a standing wave ("SW") intensity profile 813 in the axial direction 807. The beam 811 approaching the sample from the same side of the focal plane as the lens 802 can pass through the lens, if desired. For samples sufficiently thin such that only a single SW plane 814 of maximum intensity resides within the sample 810, detection and localization can proceed by axially scanning the maximum intensity plane as described above. For moderately thicker samples, the period 815 of the SW, which can be expressed as $p=\lambda \sin(\theta)/2$ (where p is the period, $\lambda$ is the wavelength of the excitation radiation, and $\theta$ is angle each beam makes with the focal plane) can be increased by decreasing the angle, $\theta$, until only a single, wider SW plane of maximum intensity intersects the sample 810. Alternatively, as shown in FIG. 8d, if several SW maxima reside within the sample 810, PTOLs 800 excited in planes corresponding to different intensity maxima 816, 817, and 818 can produce different patterned spots (e.g., spots 819 and 820 from maximum 816, spot 821 from maximum 817, and spots 822 and 823 from maximum 818) at the detector due to the differences in 2D detection point spread function that exists in different planes parallel to the plane of focus of the lens 802. For example, an image of a PTOL on the detector due to emission from the PTOL at the focal plane of the imaging optics will be smaller than an image of the PTOL due to emission from the PTOL from a plane that does not correspond to the focal plane. This information can be used to discriminate from which SW maximum a given PTOL originates. Also, the detected light can be split between M detectors in the case where M standing wave maxima reside within the sample, and corrective optics (e.g., a phase mask) can be placed between the lens 802 and each detector, such that the focal plane for each detector is coincident with a different SW maximum. Those PTOLs in focus at a given detector then can be localized in either 2D or 3D using the information recorded at that detector.

A total internal reflection ("TIRF") geometry also permits simultaneous detection and 2D localization of multiple photoactivated PTOLs in a plane. In TIRF microscopy, the intensity of excitation radiation that illuminates the sample exponentially decreases with increasing distance from the sample/substrate interface. Because of the exponential decrease of the excitation radiation as a function of distance from the sample/substrate interface, excitation that is highly localized in the z direction can be achieved with relatively little autofluorescence, especially when thick specimens are imaged. Also with TIRF microscopy, relatively few PTOLs (both activated and deactivated) are excited simultaneously for a given molecular density, so a larger density of target molecules can be initially prepared in the sample. Further, evanescent illumination at multiple angles can be used to localize the PTOLs in the z direction as well to a high degree of accuracy. Additionally, the wavelength of activation radiation as well as the wavelength of excitation radiation can be applied via an evanescent field to further reduce the extent of activated, excited PTOLs in the z direction.

Excitation radiation and activation radiation for TIRF microscopy can be delivered to the sample/substrate interface external to the objective lens using a prism that is optically coupled to the substrate. Alternatively, excitation and activation radiation can be applied to the sample/substrate interface in an epi configuration, with the excitation radiation entering at the rear pupil of the same objective lens that is used to collect fluorescence radiation emitted from PTOLs in the sample, as long as the numerical aperture ("NA") of the lens yields a maximum illumination angle, $\theta_{max} > \sin^{-1}(NA/n_{sub})$, that is greater than the critical angle for total internal reflection ("TIR") (where $n_{sub}$ is the refractive index of the substrate), and the excitation radiation enters the rear pupil in the outer annular region that supports TIR of the excitation radiation.

Figure 9A:
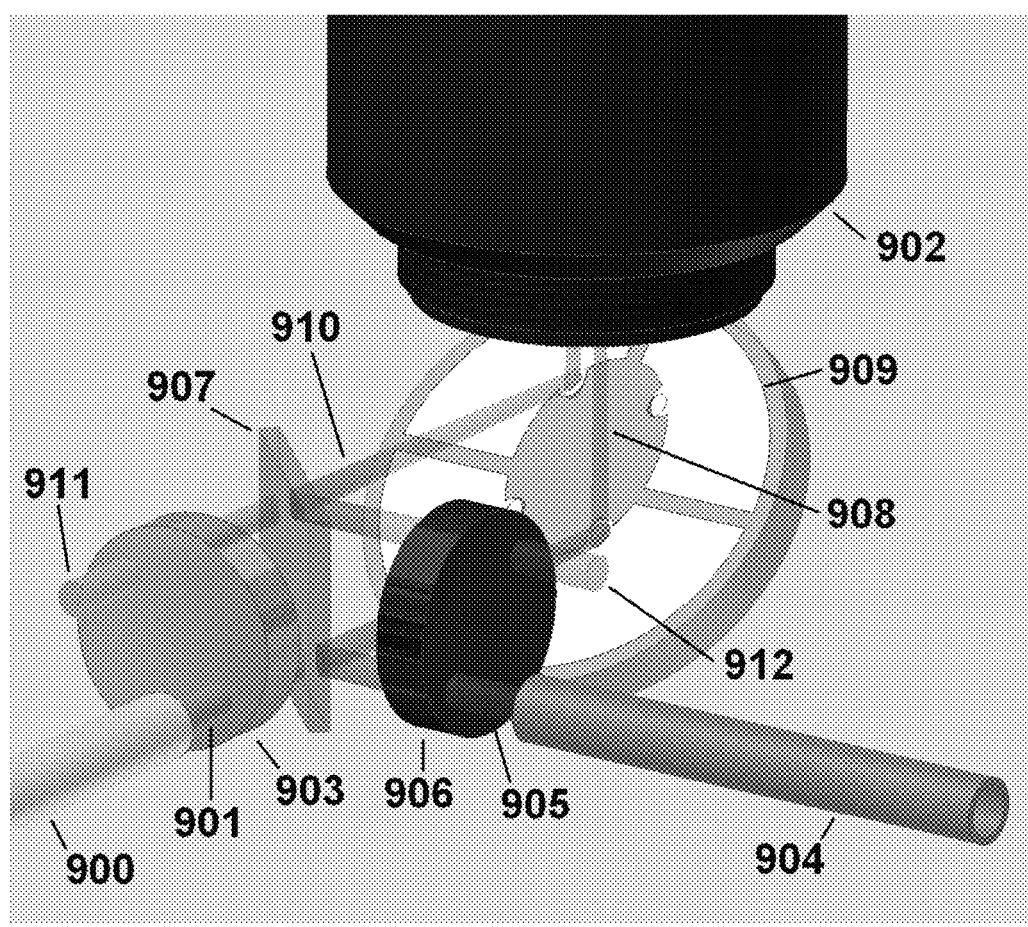
FIG. 9A is a schematic diagram of an exemplary super-resolution microscope showing the subsystem used to deliver excitation and activation radiation via total internal reflection to the sample.
Figure 9B:
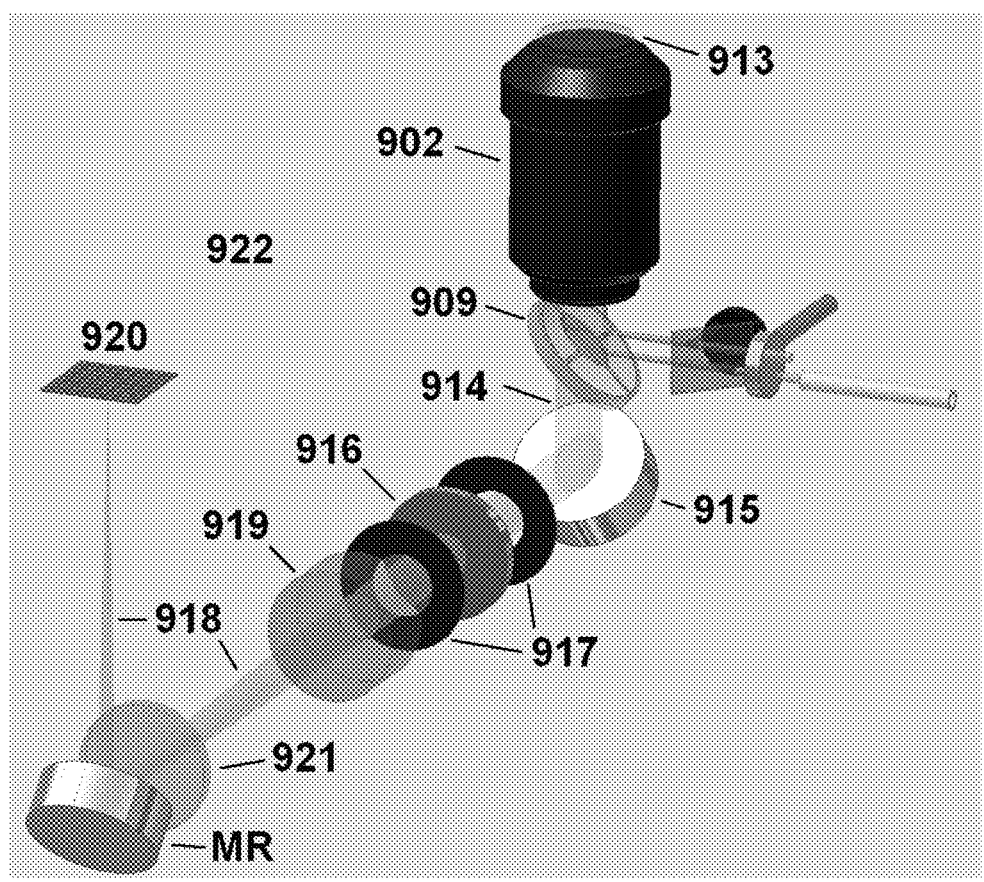
FIG. 9B is a schematic diagram of the subsystem used to detect the radiation emitted by PTOLs in the exemplary superresolution microscope of FIG. 9A.

FIGS. 9a and 9b are schematic diagrams of a system that can use through-the-objective TIRF excitation radiation to excite sparsely-populated activated PTOLs in a sample, such that radiation emitted from the activated, excited PTOLs can be imaged to produce superresolution images of the sample via phototransformation, isolation, and localization of multiple subsets of discrete PTOLs within the sample. For continuous excitation of activated PTOLs, light having a wavelength of 561 nm emitted from a 10 mW diode-pumped solid-state laser (available from Lasos GmbH, Jena, Germany) is fiber-coupled to an excitation collimator 900 and provides an excitation input beam 901 that can be focused at the rear pupil plane internal to a 60×, 1.45 NA total internal reflection fluorescence ("TIRF") oil immersion objective 902 (available from Olympus America, Melville, N.Y.). A narrow bandwidth laser line filter 903 (available from Semrock, Inc., Rochester, N.Y.) is used to reject both emission noise from the laser and autofluorescence generated in the optical path prior to the objective 902. For pulsed activation of the PTOLs, a second diode laser (available form Coherent Inc., Santa Clara, Calif.) that can yield about 50 mW of power at an activation wavelength, $\lambda_{act}$, of about 405 nm can be fiber-coupled through an intermediate galvanometer-based switch (not shown) to an activation collimator 904 to create a focused activation input beam 905 that is similarly filtered by a bandpass filter 906 (available from CVI Optical, Covina, Calif.) before being combined with the excitation input beam 901 at a dichroic mirror 907 (available from Semrock, Inc.). This combined input beam 908 then can be reflected from an elliptical spot on a custom-patterned, aluminized mirror 909 (available from Reynard Corp., San Clemente, Calif.) into the objective 902. The radius, $\rho$, at which the combined beam 908 enters objective 902 can be controlled to be $(n_{sample}/NA)*4.35 \approx 4.14$ mm$\leq \rho \leq$4.35 mm (for $n_{sample} \approx 1.38$), such that the resulting refracted ray transverses a low autofluorescence immersion oil (e.g., Cargille type FF, available from Structure Probe Inc., West Chester, Pa.) and is incident at the interface between the sample and a cover slip 913 (e.g., a #2 thickness cover slip available from Fisher Scientific, Hampton, N.H.) at greater than the critical angle, $\theta_c \approx \sin^{-1}(n_{sample}/n_{coverslip})$ for which total internal reflection ("TIR") occurs. An evanescent field can be thereby established within the sample, exciting only those molecules within the short decay length of the evanescent field. A substantial proportion of the incident energy of the excitation and activation beams, however, can be reflected at the interface to yield a combined output beam 910 that emerges from the objective 902, and that is then reflected from a second elliptical spot on mirror 909 diagonally opposite the first elliptical spot on the mirror. This beam 910 is then divided at dichroic mirror 907 into an excitation output beam 911 and a separate activation output beam 912 that are finally directed to respective beam dumps.

For typical molecular cross-sections (e.g., approximately $10^{-16}$ cm$^2$), the reflected excitation beam energy may be $10^{15}$-fold more intense than a PTOL signal beam 914 that emerges from the objective 902, as shown in FIG. 9b. Therefore, a challenge in this through-the-objective TIRF geometry is the isolation of the molecular signal from both the interface-reflected excitation beam and any autofluorescence generated by this beam in the optics encountered thereafter. The mirror 909 aids in this isolation because the mirror has an elliptical, anti-reflection coated, transmissive aperture whose projection perpendicular to the objective axis matches the 8.7 mm diameter of the rear pupil, and therefore passes signal beam 914 to the detection optics with high efficiency. Also, for an elliptical reflective spot D times larger than the gaussian width of the reflected beam at the spot, only about erfc(D) of the excitation energy is passed onto the detection optics, or ~$2 \cdot 10^{-5}$ to ~$2 \cdot 10^{-8}$ for D=3 or 4, respectively. Furthermore, since the spots occlude only a small fraction of the periphery of the rear pupil, they do not substantially degrade the detection numerical aperture. Consequently, the PSF standard deviation, s, that factors into sub-diffraction limited localization of PTOLs is not substantially degraded. Furthermore, the mirror 909 is wavelength insensitive, and therefore can be used with different excitation lasers and different PTOLs without replacement. The mirror 909 can include multiple spots to support multi-angle, multi-polarization and/or standing wave TIRF excitation.

After passage through custom spotted mirror 909, the largely collimated signal beam 914 emerging from the infinity-corrected objective 902 can be reflected by a first mirror 915 (as shown in FIG. 9b) to travel along the axis of the detection optics. Any remaining excitation light (as well as much of the remaining activation light) traveling substantially along this axis can be removed by a Raman edge filter 916 (available from Semrock, Inc.). However, because the optical density of this filter 916 decreases rapidly with increasing deviation from normal incidence, baffles 917 can be placed on either side of the filter to remove scattered light at higher angles of incidence generated elsewhere within the system. The filtered signal beam can be focused into a focused beam 918 with an acromatic tube lens 919 (available from Edmund Optics, Barrington, N.J.) onto the face of a back-illuminated, thermoelectrically cooled (e.g., to −50° C.), electron multiplying CCD camera 920 (available from Andor Scientific, South Windsor, Conn.) to create the desired image of isolated single molecules. A 405 nm notch filter 921 (available from Semrock, Inc.) also can be included to further insure that the camera 920 is not saturated when the activation beam is applied.

Figure 10A:
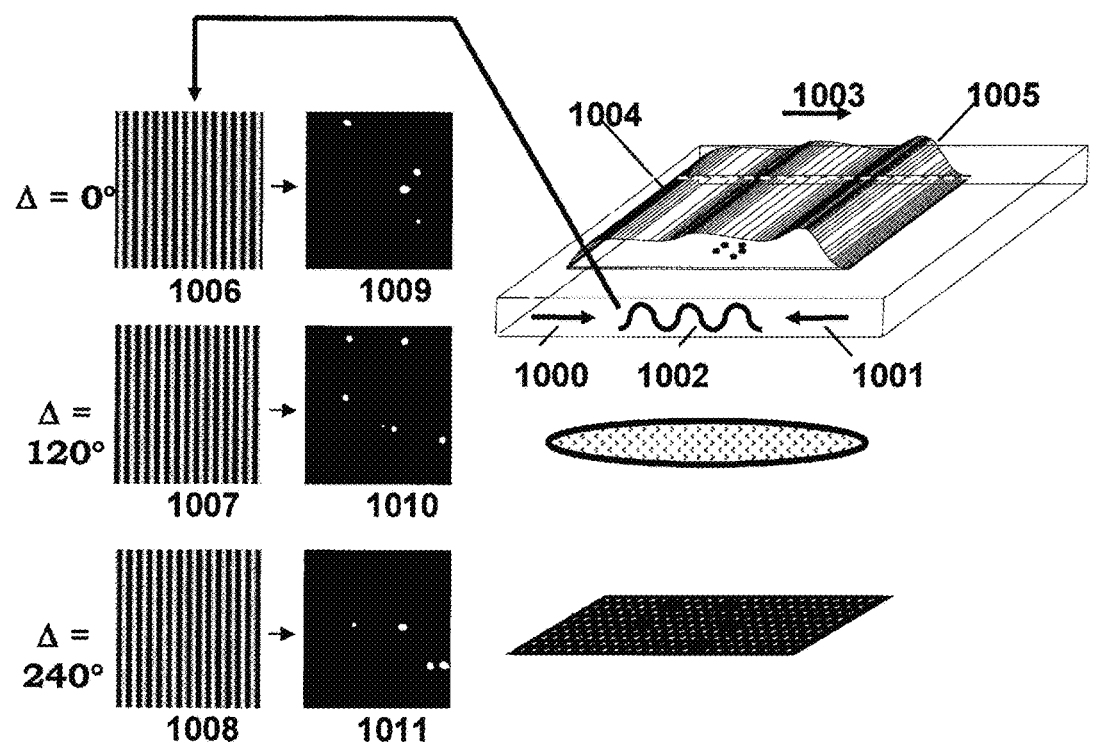
FIG. 10A is a schematic diagram illustrating the use of excitation radiation structured in a plane parallel to the focal plane of a lens in order to provide improved localization precision for individual PTOLs.
Figure 10B:
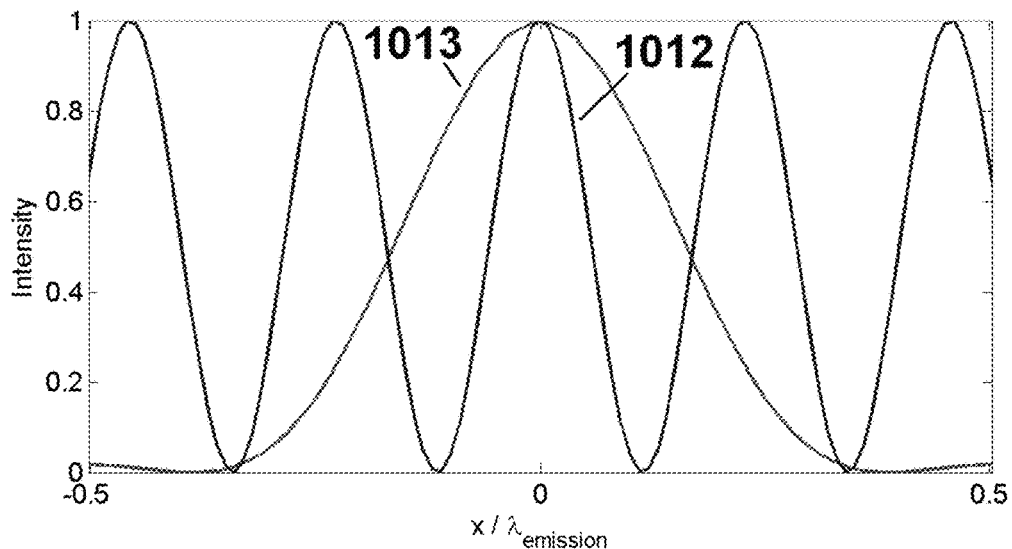
FIG. 10B compares detection-based and standing wave excitation-based point spread functions useful for localizing individual PTOLs.

To further increase the localization accuracy in the plane of the sample/substrate interface in the TIRF configuration the substrate can be used as a waveguide to support the propagation of two or more intersecting excitation beams. These beams then can form a structured excitation field within this plane that is evanescent perpendicular to the interface. For example, as shown in FIG. 10a, two such excitation beams 1000 and 1001 can create a standing wave ("SW") intensity profile 1002 along one axis 1003 parallel to the interface between the sample 1004 and the substrate 1005. Scanning this SW over one period along this axis (e.g., at phases, Δ=0° (as illustrated in frame 1006), Δ=120° (as illustrated in frame 1007), and Δ=240° (as illustrated in frame 1008)) and capturing images (e.g., as shown in frames 1009, 1010, and 1011) of the activated PTOLs at each SW position then can allow the PTOLs to be localized on the basis of an effective excitation PSF 1012 as shown in FIG. 10b, having a width $\sim \lambda_{exc}/(4 n_{sub})$ where $\lambda_{exc}$ is the wavelength of the excitation radiation and $n_{sub}$ is the index of refraction of the substrate, which is lower than the detection PSF 1013 having a width $\sim \lambda_{ems}/(2\ NA)$ present at the CCD, where $\lambda_{ems}$ is the wavelength of signal radiation emitted from PTOLs. The PSF is especially improved when high $n_{sub}$ substrates can be used. A second SW orthogonal to the first then can be generated and scanned over the same subset of activated PTOLs to localize them along the other axis within the plane.

Figure 10C:
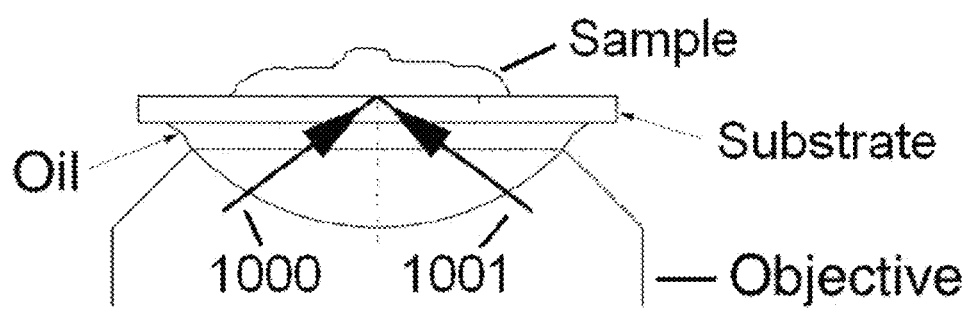
FIG. 10C illustrates the generation of a standing wave at a total internal reflection interface between a sample and a substrate by using two counter-propagating coherent beams that pass through an imaging objective.

The beams 1000 and 1001 forming a TIRF excitation field structured in the plane of the interface also can be transmitted to the interface either through a TIRF-capable signal collection objective (as shown in FIG. 10c), or with optical elements (e.g., prisms) on the side of the substrate opposite the interface.

Widefield molecular localization is well suited to thin samples (to reduce out-of-focal plane fluorescence), and TIRF molecular localization is suited to portions of the sample near the sample/substrate interface, by the evanescent field. On the other hand, confocal microscopy can be used to localize PTOLs in 3D in thick samples, such as whole cells. The 3D confocal overall PSF, defined by the product of the excitation PSF (determined by focusing of the excitation) with the 3D detection PSF (defined by the confocal pinhole and the numerical aperture of the detection objective), can be volumetrically larger than in the thin sample widefield or TIRF cases. Therefore, autofluorescence may be larger in such a case, which can reduce the localization accuracy or suggest the use of PTOLs having higher intrinsic brightness.

However, activation and excitation energy outside the focal plane in the incoming and outgoing focal cones of the confocal microscope can prematurely activate and then photobleach PTOLs, adding to the out-of-focus background and reducing the population of PTOLs that can be accurately localized (i.e, those near the focal plane)). Since many of the photoswitchable FPs (e.g., PA-GFP and Kaede) are activated by violet or near-UV light, this problem can be lessened by using multiphoton excitation to activate the molecules, since this nonlinear process generally results in low PTOL activation outside the effective multiphoton depth of focus. The multiphoton focus could either precede the confocal excitation focus during the latter's path through the scan volume, or molecules across the current focal plane could first be activated by a 2D scan of the multiphoton focus until the desired density of individually resolvable activated molecules is reached, to be followed by a similar 2D scan of the confocal focus to detect and localize the molecules so activated. Also, when multifocal activation is used, damage to the specimen from the short wavelength of the activation beam is likely to be greatly reduced.

Confocal molecular localization is a serial process, and therefore relatively slow. For example, confocal molecular localization is a triply serial process because it provides activation, followed by acquisition of multiple serially scanned 3D images until all currently activated molecules are bleached, followed again by activation and multiple 3D scanning—over and over again, until a 3D map of molecular positions of the desired density is obtained. This is obviously a slower proposition than 2D imaging by widefield or TIRF molecular localization. Multifocal microscopy utilizing Nipkow disk technology can be used to increase the speed of the process to some extent, but it creates multiple foci only in a single plane, and still generates significant out-of-focal plane excitation leading to premature bleaching of target molecules and increased autofluorescence-induced background, even with pinhole filtering. On the other hand, 3D lattice excitation can provide many excitation maxima simultaneously in 3D, as described in PCT Patent Application Serial No. PCT/US2005/042686 Nov. 23, 2005, and entitled "OPTICAL LATTICE MICROSCOPY," which is incorporated herein by reference, with unintended photobleaching and associated background significantly reduced by the improved confinement of the excitation to predominantly these maxima alone. Furthermore, if the lattice is created with constituent beams spread across a greater solid angle than that covered by a single microscope objective, the confinement of the excitation at each lattice maximum (e.g., as defined by the full volume at half peak intensity) can be greater than that in either single focus or traditional multifocal microscopy, further reducing the background signal significantly, and permitting more accurate localization of each PTOL, due to the tighter initial PSF. Of course, an optimal SNR and initial PSF is expected when all beams of the maximally symmetric composite lattice are used. As in the confocal case, multiphoton activation can be locally applied, such as with a multiphoton lattice, either scanned ahead of the fluorescence excitation lattice, or scanned to create a series of parallel planes of activated PTOLs prior to simultaneous scanning of these planes by the fluorescence excitation lattice.

d. PTOL Properties

PTOLs useful for superresolution via localization of isolated PTOLs generally have one or more of the following distinguishing characteristics: a relatively high brightness (as defined by its excitation cross section and the quantum efficiency); a relatively high contrast ratio between luminescence generated in the activated state to that generated in the inactivated state (which might be improved through a judicious choice of the excitation wavelength and detection filter set); an excitation wavelength that reduces autofluorescence from other cellular material exposed to the excitation; an emission wavelength that is sufficiently different from the spectral range over which most autofluorescence occurs; and photostability that is large enough that a sufficient number of photons are collected from each PTOL to achieve the desired localization accuracy prior to irreversible bleaching, yet, for PTOLs other than the kindling proteins and Dronpa that can switch back to the deactivated state, is nevertheless still finite, so that a new population of individually resolvable activated PTOLs can be created after the current set is largely bleached. Indeed, to reduce possible phototoxicity related to irreversible photobleaching, an ideal PTOL would remain in the activated state until it is deactivated by choice using other means (e.g., illumination at a separate deactivation wavelength).

Superresolution via localization has been demonstrated with the tetrameric PTOLs Kaede and Kikume, as well as the monomeric, dimeric, and tandem dimer forms of EosFP. These PTOLS have the common advantages of large wavelength spread between the inactivated and activated absorption and emission maxima, high brightness, and longer wavelength emission, where autofluorescence is typically lower. Monomeric EosFP has the added advantage of smaller physical size than tetrameric Kaede or Kikume, and may therefore be less perturbative of cellular structure and function. In practice, a particular FP could be selected from a number of different FPs based on a user's criteria for optimization for a given application.

e. Background Reduction

If the contrast ratio between activated and inactivated PTOLs is too low at a given initial density of target PTOLs to achieve the desired SNR and consequent localization accuracy, the contrast ratio can be improved by irreversibly bleaching a portion of the target PTOLs until the effective molecular density and resulting SNR is as desired. Other autofluorescent material in the sample can also be prebleached using the excitation light without affecting the bulk of the inactivated PTOLs. Further discrimination with respect to background might be obtained via appropriate spectral filtering, fluorescence lifetime measurements, or polarized excitation and/or polarization analyzed detection.

In widefield microscopy, spatially structured activation energy concentrated near the focal plane (e.g., from an axial standing wave) can be used to reduce the background from activated, out-of-focus PTOLs away from this plane. In confocal or lattice microscopy, similar background reductions can be achieved with standing wave or other means of planar, axially structured activation rather than the 3D confined foci traditionally applied by these methods.

f. Polarized Excitation/Detection

Light from PTOLs having an electric dipole moment located in a sample can be detected and imaged using the techniques described herein. When such PTOLs have a fixed spatial orientation in the sample, they can be selectively activated, excited, and/or imaged with polarized light. By analyzing the polarization of the light emitted from such PTOLs (e.g., by passing light emitted from such PTOLs in the sample through a polarization filter prior to detecting the light such that only light having a desired polarization is detected) the dipole orientations of these PTOLs can be determined. For a plurality of fixed dipole PTOLs that are randomly oriented in a sample, the PTOLs can be activated and/or excited with equal probability by using activation and/or excitation radiation polarized in all three orthogonal directions, rather than with the unequal weightings that would result from using activation and/or excitation radiation having a single excitation polarization. Because the electric field of a polarized light lies in a plane orthogonal to its direction of propagation, polarized excitation in all three directions requires at least two independent excitation beams. For example, the through-the-objective TIRF system described herein, inter alia, with respect to FIG. 9 is capable of delivering four independent beams at 90° intervals in the plane of the sample/substrate interface, by using four excitation collimators 900, creating four input beams 901 that are reflected from four spots on mirror 909 and sent into the rear pupil of objective 902. Polarizing the beams at 0° and 90° radially with respect to the rear pupil and similarly polarizing the beams at 180° and 270° azimuthally results in two interfacial waves, polarized orthogonally with respect to one another in the plane of the interface, and two interfacial waves polarized orthogonal to the interface. These beams can be turned on either sequentially or simulataneously—although in the latter case, beams having common polarization vectors will mutually interfere. In fact, as shown in FIG. 10, by turning on the beams in pairs with like polarization, a standing wave can be formed to provide enhanced localization accuracy due to the sharp excitation PSF of the standing wave. Thus, the features of accurate localization, dipole determination, and equal excitation probably of fixed dipoles can be combined.

g. Exemplary Superresolution Images

Figures 11A, 11B:
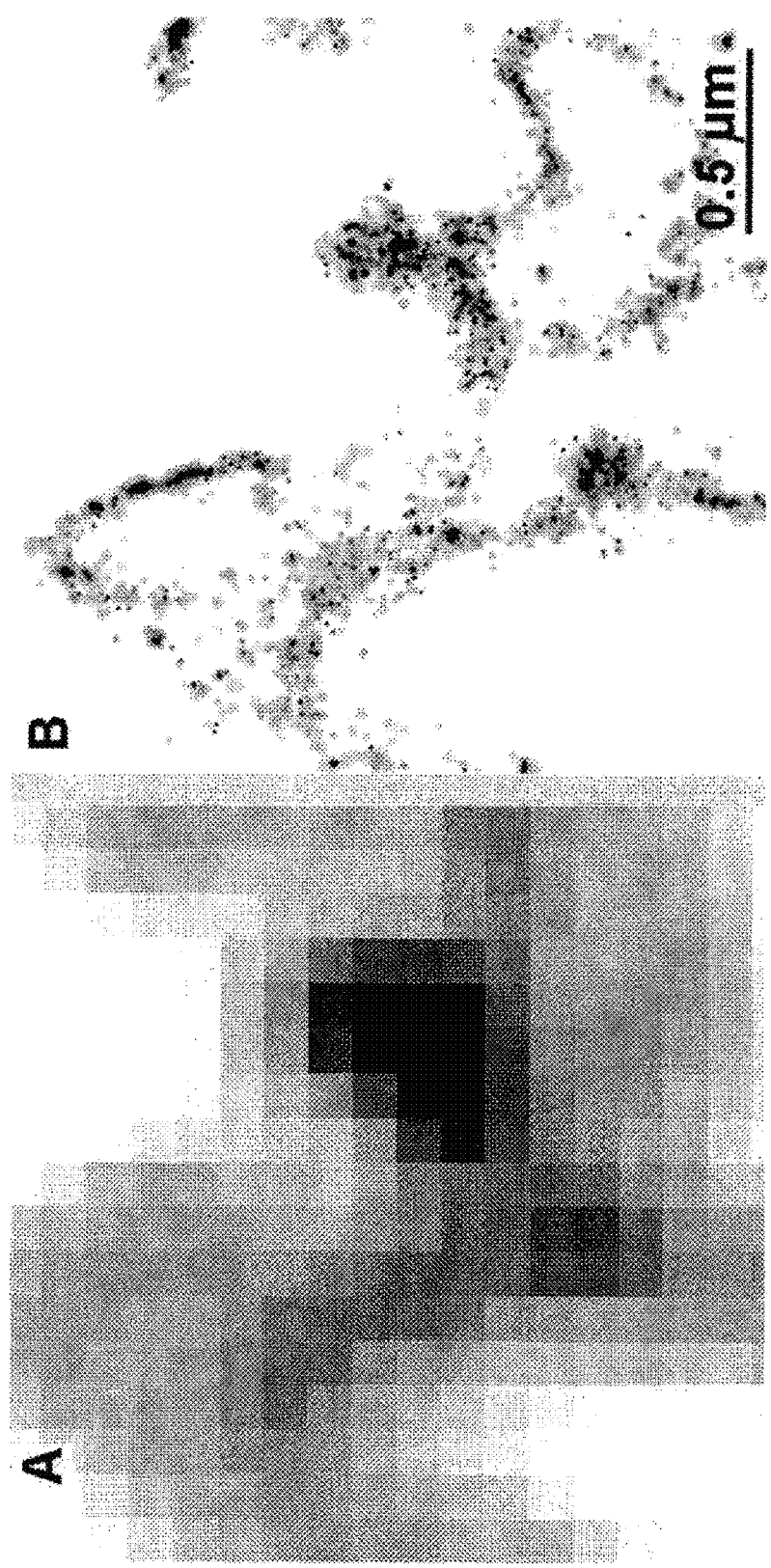
FIG. 11A is a conventional total internal reflection image of a thin section through several lysosomes in a cell, made visible by fluorescence from a PTOL-tagged, lysosome-specific transmembrane protein.
FIG. 11B is a superresolution image of the same area of the same section, obtained by isolation and precise localization of individual PTOLs.

FIG. 11 compares a diffraction-limited image (FIG. 11*a*) of a lysosomal structure in a COS7 cell and superresolution image (FIG. 11*b*) of the same lysosomal structure in the same COS7 cell, which was obtained using the apparatus and techniques of TIRF isolation/localization described herein. The sample containing the COST cell was prepared by transient transfection with a plasmid designed for the expression of the photoactivatable protein Kaede fused to the lysosomal transmembrane protein CD63. Cells were pelletized and then sectioned with a microtome, using the techniques common to transmission electron microscopy, to create the approximately 80 nm thick section that was imaged. 20,000 frames of single molecule images were taken, with activation energy applied in a brief pulse after every 20 frames to restore the number of activated molecules to a higher, but still individually resolvable level. The superresolution image shown in FIG. 11b was formed from more than 51,000 isolated molecules, with each molecule localized with an uncertainty of 24 nm or less redrawn in FIG. 11b as a spot having an intensity image profile given by a Gaussian distribution with a standard deviation equal to the position uncertainty. The profiles of the spots for each molecule were normalized to provide the same integrated intensity for each molecule. Thus, more highly localized molecules appear as bright, sharp dots, and less well localized ones appear broad and dim. The diffraction limited image was formed by summing the diffraction limited images of the same set of isolated molecules, and was verified to be indistinguishable from the conventional TIRF image.

FIG. 12 compares a diffraction-limited image (FIG. 12a) obtained at the interface of a whole, fixed fox lung fibroblast cell and a glass cover slip in phosphate buffered saline and a superresolution (FIG. 12b) image of the same fox lung fibroblast cell. The cell was transiently transfected to express the photoactivatable protein dEosFP fused to the cell attachment protein vinculin. The images were created in the same manner as described in conjunction with FIG. 11. The diffraction limited image highlights a single focal adhesion region at the periphery of the cell, and the superresolution image by PTOL localization shows a magnified view of the structure within the box in FIG. 12a.

3. Enhanced Resolution Via Overlapped Spatially Structured Activation and Excitation The overall PSF of any form of optical microscopy (e.g., widefield, TIRF, confocal, or lattice) is typically given by the product of the excitation PSF with that of the detection PSF (i.e., $PSF_{overall} = PSF_{excitation} \times PSF_{detection}$). Widefield microscopy offers no excitation contribution to the resolution, traditional TIRF microscopy offers very high z-axis excitation resolution, but none in the x- and y-axes, and both confocal and lattice microscopy contribute excitation resolution by concentration of the excitation field to either a single focus, or a lattice of intensity maxima.

PTOLs offer a way of contributing a third component to the overall PSF by confining the activation illumination to a localized region in a manner similar to that used to confine the excitation energy itself (i.e., $PSF_{overall} = PSF_{activation} \times PSF_{excitation} \times PSF_{detection}$). Thus, for example, a focused activation beam can be temporarily applied at the focal point of a confocal microscope, followed by a focused beam at the excitation wavelength for the activated PTOLs, with the resulting emission being detected confocally in a spatially localized manner. This process can then be repeated over many voxels (i.e., a 3D pixel) to create a complete superresolution 3D image. One caveat is that the number of activated PTOLs in a focal volume should decline significantly (either by irreversible photobleaching, or reversion to the unactivated state) before activation and excitation is applied to an immediately neighboring voxel, or else the effective activation PSF will be reflective of the larger region defined by the overlapping, neighboring activation foci, thereby degrading the effective overall PSF. Dronpa appears to be a particularly good candidate for this method of superresolution, because the activated molecules are returned to the deactivated state by the process of their excitation, thereby providing a natural means to depopulate the activated ensemble while simultaneously determining when the scan should proceed to the next voxel. If the deactivation occurs too quickly, multiple activation/(deactivation and measurement) cycles can be performed at the same position before proceeding to the next position. Using Dronpa as the PTOL in this process allows more than about 100 such cycles to be performed at each position.

Figure 13A:
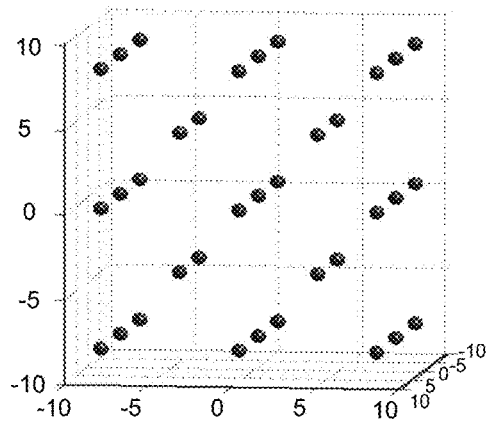
FIG. 13A is a plot of an activation optical lattice at an activation wavelength for a given PTOL species.
Figure 13D:
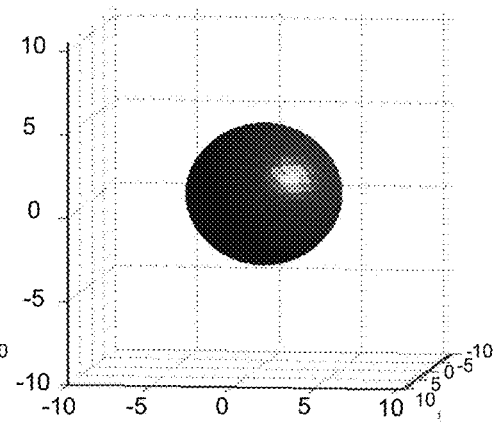
FIG. 13D is a plot of a single intensity maximum within the activation lattice in FIG. 13A.
Figure 13B:
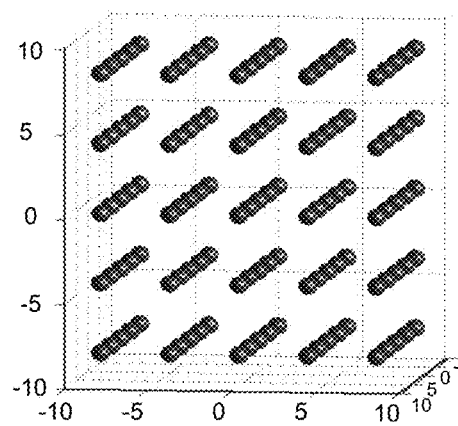
FIG. 13B is a plot of an excitation optical lattice at an excitation wavelength for the given PTOL species.
Figure 13E:
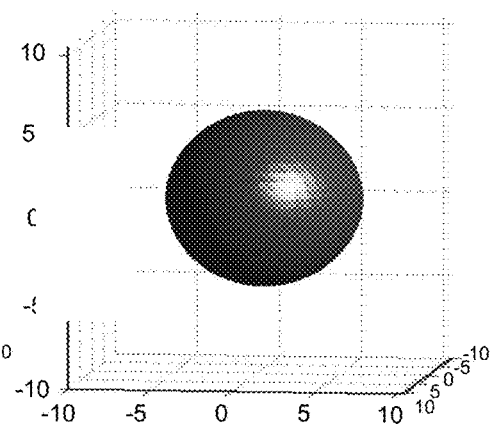
FIG. 13E is a plot of a single intensity maximum within the excitation lattice in FIG. 13B.
Figure 13C:
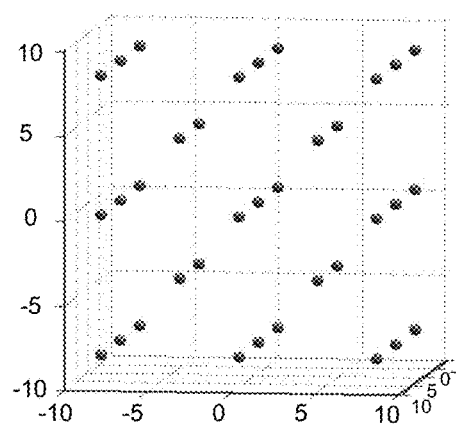
FIG. 13C is an effective overall signal producing lattice based on the overlap of the activation and excitation lattices in FIGS. 13A and B, respectively.
Figure 13F:
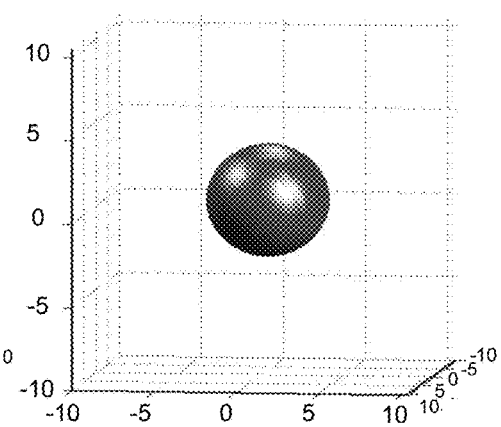
FIG. 13F is a plot of a single effective overall signal generating region within the overall signal producing lattice in FIG. 13C.

Because the activation wavelength is typically short (e.g., about 400 nm) for Dronpa, the activation PSF can provide most of the resolution benefit in the overall PSF. If cellular damage from this short of a wavelength is a concern, multiphoton activation can be used, at the cost of a slightly larger activation PSF than is possible with linear (i.e., single photon) activation. In addition, because the density of emitting molecules is given by $PSF_{activation} \times PSF_{excitation}$, the emitting molecules will be confined to at least as tight a focal region as in conventional two-photon excitation, thereby leading to greatly reduced out-of-plane photobleaching and background, even using linear, confocal excitation. Of course, further gains in both spatial and temporal resolution are possible if sparse composite lattices of the same or commensurate periods are used for both the activation radiation (as shown in FIG. 13a, and in the close up view of FIG. 13a shown in FIG. 13d) and for the excitation radiation (as shown in FIG. 13b, and in the close up of FIG. 13b in FIG. 13e), leading to an overall lattice (shown in FIG. 13c) that achieves activation and excitation of PTOLs and that has having sharper maxima (shown in FIG. 13f) than the maxima in the lattices for the activation and excitation radiation. Point spread function engineering and relative displacement of the activation and excitation PSFs might be used to further increase the resolution by reducing the region of their effective overlap. If the contribution of the detection PSF to the overall resolution is negligible, it might be advantageous to simply omit pinhole filtering (as in most embodiments of multiphoton microscopy) in order to maximize the collected signal. Finally, we note that this method of superresolution, is well suited to dynamic superresolution imaging in living cells (particularly with lattice microscopy), because potentially many more molecules would be emitting photons at a given time from each focus (when confocal radiation is used for activation and excitation) or excitation maximum (when radiation patterned in a lattice is used for activation and excitation).

4. Superresolution Via Saturated Deactivation

By exploiting the saturation of the deactivation of PTOLs over a sub-portion of a diffraction-limited focal volume in which a portion of the PTOLs were previously activated, one can collect emission from a sub-diffraction limited region, and then repeat at multiple locations to generate a sub-diffraction limited image. This concept is described in FIG. 14 in reference to activation, deactivation, and excitation with optical lattices, although other means (e.g., single focused beams) can also be employed.

Figure 14A:
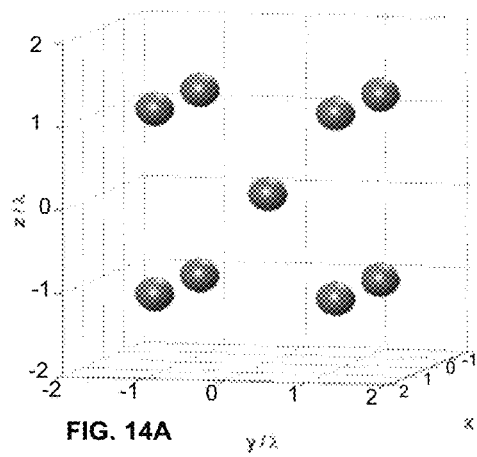
FIG. 14A is a plot of an activation optical lattice at an activation wavelength for a given PTOL species.
Figure 14D:
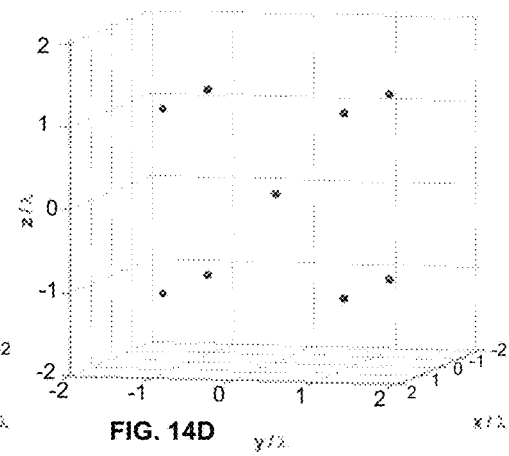
FIG. 14D is an effective overall signal producing depletion lattice based on the overlap of the activation, deactivation, and excitation lattices in FIGS. 14A-C, respectively.
Figure 14B:
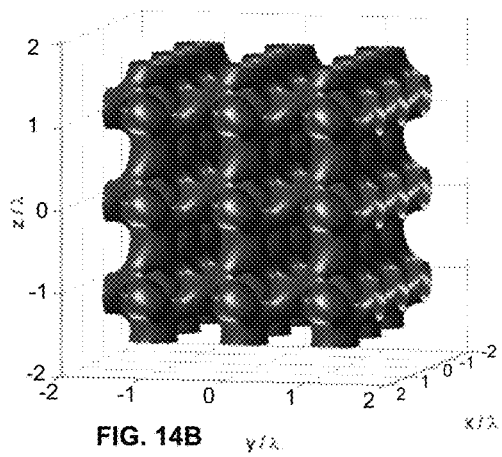
FIG. 14B is a plot of a deactivation optical lattice at a deactivation wavelength for the given PTOL species, consisting of a deactivating intensity shell with a central node at each lattice point.
Figure 14E:
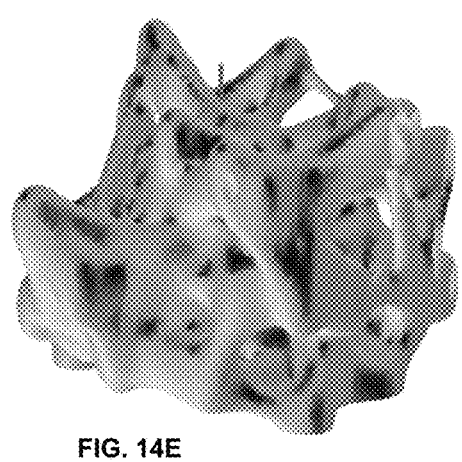
FIG. 14E is a virtual image of a 3D test object obtained by the depletion lattice in FIG. 14D.
Figure 14C:
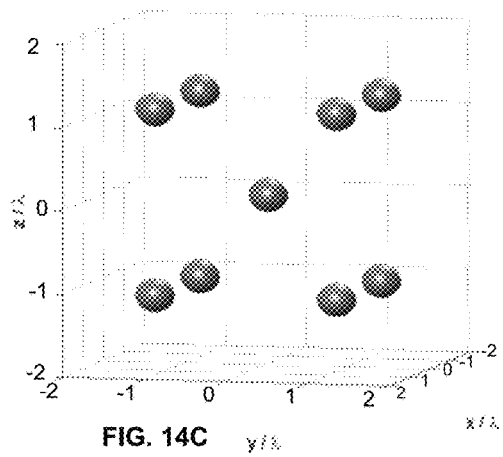
FIG. 14C is a plot of an excitation lattice at an excitation wavelength for the given PTOL species.
Figure 14F:
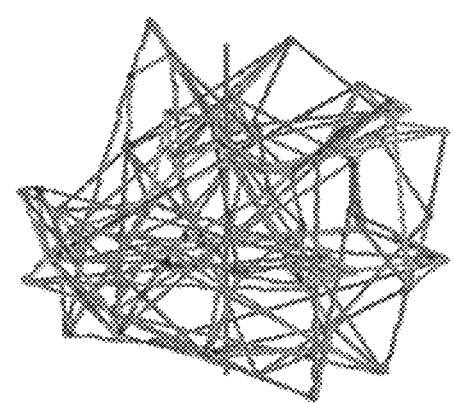
FIG. 14F is a virtual image of the same 3D test object obtained by conventional confocal microscopy.

As shown in FIG. 14a, a lattice of confined intensity maxima can be first created at the activation wavelength of the PTOLs to create an array of localized regions of activated PTOLs. Next, a depletion lattice (as shown in FIG. 14b) having a central low intensity node within a shell of high intensity located at each lattice point, can be applied at a wavelength that returns the PTOLs outside each node to their unactivated state. Next, an excitation lattice (as shown in FIG. 14c) can be applied at the excitation wavelength of the activated PTOLs, so that the small (e.g., having dimensions that can be less than the wavelength of the emission radiation) volume of PTOLs near each node of the depletion lattice is excited and then emits photons, resulting in the desired lattice of superresolution foci (as shown in FIG. 14d). Next, the remaining activated PTOLs are deactivated, such as by exciting them until a substantial fraction of them photobleach, or by applying a deactivation radiation until a substantial fraction of them are returned to the unactivated- .state. This process of activation, partial deactivation with a nodal pattern, excitation, and nearly complete deactivation can then be repeated at different points to create a lattice of superresolution foci offset from the first. By repeating the process further at a multiplicity of points across each primitive cell of the lattice, and detecting emission radiation from individual superresolution foci in a given cycle of activation/ nodal deactivation/excitation/complete deactivation at separate detection elements (e.g., the pixels of a CCD detector), a complete 3D image can be constructed (as shown in FIG. 14f), at considerably higher resolution than is possible, for example, by conventional confocal microscopy (as shown in FIG. 14e). All three lattices (i.e., the lattices of the activation radiation, the depletion radiation, and the excitation radiation) can be chosen at wavelength-normalized periodicities, such that the ratios of their absolute periodicities form simple integer fractions (i.e., i/j), or ideally, have the same absolute periodicity (i/j=1), so that many of the activation maxima, deactivation depletion shells, and excitation maxima overlap. The completely deactivating radiation can also be applied in the form of a lattice, or as a substantially uniform deactivation field.

Again considering more general radiation patterns, it is important to note that only the nodal deactivation radiation pattern needs to be spatially structured (specifically, with at least one low intensity node), and that even uniform activation, excitation, or complete deactivation radiation fields may be applied. However, it may be beneficial to spatially structure either or both of the activation and excitation fields as well, in order to increase the contrast between the desired remaining activated PTOLs near the nodes after deactivation relative to undesired remaining activated PTOLs elsewhere, and to reduce the potential damage to reversible PTOLs by repeated activation and deactivation cycles. More thorough final deactivation near the nodes may also be attained by spatially structuring the complete deactivation radiation as well, to concentrate it at these points of residual activation. Also note that the density and spatial confinement of the activated PTOLs remaining after application of the deactivation energy is improved if the deactivation field is closer to zero intensity at the nodes, and if the rate of decrease in deactivation intensity near the nodes is high.

Specific photoactivatable FPs can be used in this technique. For example, kindling proteins, such as KFP1 and dronpa, can be used because they both can be photoswitched back to an unactivated state. KFP1 requires low intensity activation to insure that the molecules are not irreversibly activated, has a relatively low quantum efficiency, and deactivation of KFP1 occurs at a different wavelength than the excitation. Dronpa exhibits high brightness and is demonstrably switchable over many cycles, but time gating of the detection signal is required, because the depletion wavelength is the same as the excitation wavelength, so the fluorescence generated during depletion of the activated state must be rejected, or collected separately from the later emission near the depletion nodes. On the other hand, the emission collected during depletion can be used to generate a high SNR diffraction-limited image, since many more molecules would contribute to the emission during depletion.

5. PTOL Imaging at Reduced Temperatures

Biological samples labeled with PTOLs that are alive or at room temperature pose special challenges for this localization microscopy. The PTOL labels might diffuse or be transported beyond the localization accuracy during the relatively long multi-frame acquisition time. In addition, other properties such as the PTOL orientation could be varying during the acquisition resulting in the loss of potentially useful microscopic information. Thus, cooling a sample below room temperature can reduce the movement of a sample while it is imaged.

Figure 15:
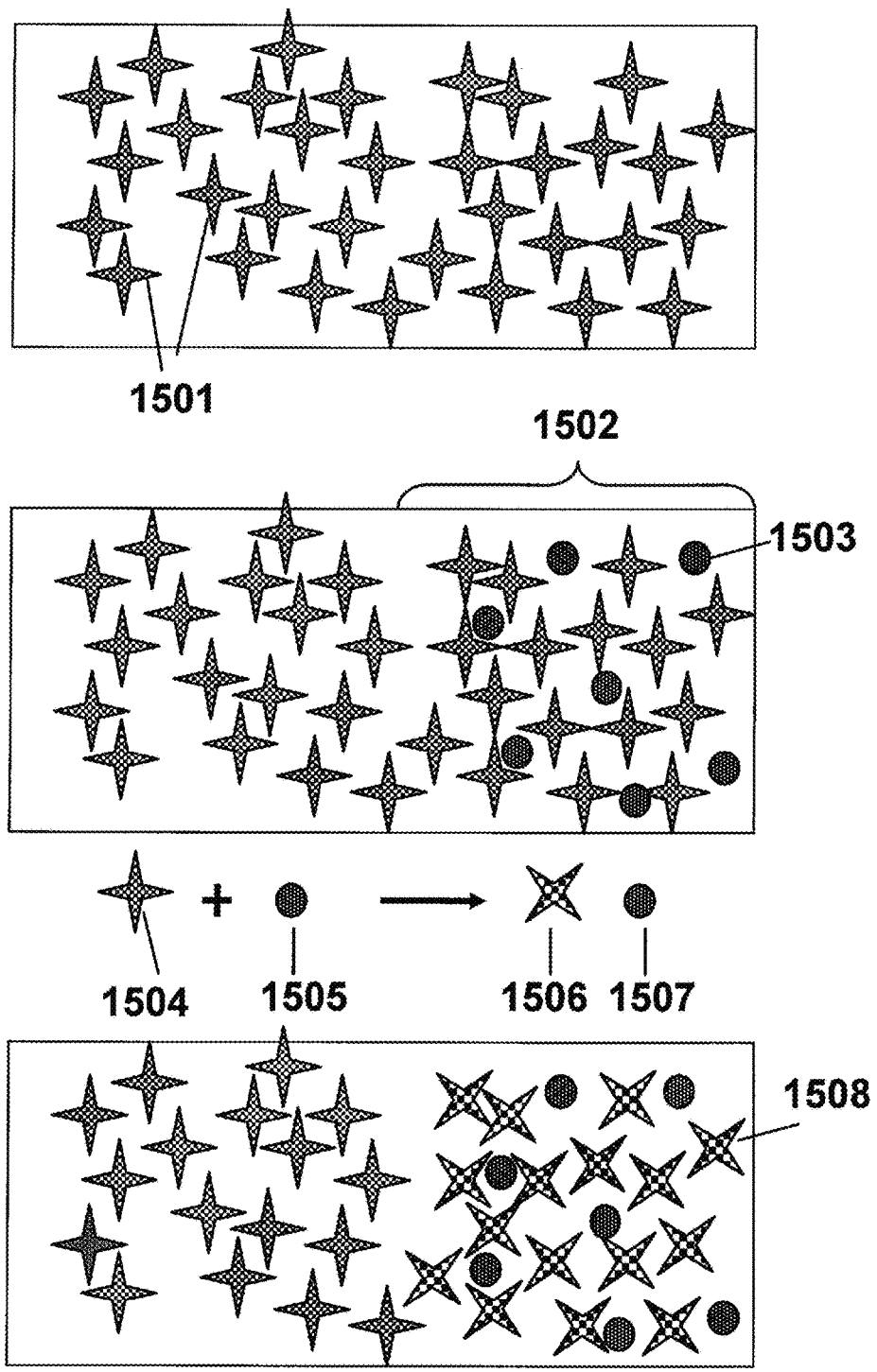
FIG. 15 is a schematic diagram of how a sub-diffractive limited latent image can be rendered using PTOLs. In this example PTOLs are embedded in a chemically amplified resist. Exposure of part of the area of the resist to a patterning beam can release acids in that area. Such acids in turn can change the optical properties of the neighboring PTOLs.

In addition, at reduced temperatures, the brightness and spectral line widths of certain PTOLs improve, so that more photons can be acquired more quickly for better resolved localization images, and contrast of the PTOLs relative to autofluorescence background may be reduced. Included here is an implementation where the sample or the sample and parts of the microscope is cooled below freezing temperatures to mitigate these limitations. In particular, rapid freezing can prepare samples in a vitreous state so that no potentially damaging ice crystals are formed within the sample 6. PTOL Microscopy of Latent Images In lithography, nanometer scale patterns can be written with photon, electron, ion or atom beams. Typically the pattern is written onto a beam sensitive material such as a resist. In the cases of optical or electron beams, photoresist or e-beam resists can be used. For optimal lithographic performance it is useful to characterize the precise shape of the beam and the exposed pattern at an early stage before subsequent processing transfers the exposed resist pattern onto other materials. Thus, a resist can contain PTOLs or be labeled with PTOLs on the top or bottom surfaces of the resist layer. In this case, contrast can be imposed by the exposing beam by several kinds of exposure beams, and the exposure beam can have a detectable effect on the PTOLs in the resist, such that imaging the PTOLs after exposure can reveal the pattern of the exposure beam in the resist. For example, such an exposure beam can: destroy a PTOLs ability to radiate (e.g. by electron beam ionization, or UV induced bond breaking, etc.); shift the emission wavelength of the PTOL (e.g., in a manner similar to the wavelength shift in Kaede due to activation radiation); or catalyze the release of an acid in the resist, as is common in the case of chemically activated resists, which then changes the photophysical properties of the exposed PTOLs. Thus, as shown in FIG. 15a, to resist can include a number of PTOLs. As shown in FIG. 15b, when a portion 1502 of the resist is exposed to exposure radiation in a lithography process, photo-lithographically activated acids 1503 can catalyze further cleavage or polymerization of resist. In addition, the acids 1503 can also shift the emission wavelength of the PTOLs (e.g., when Eos is used as the PTOL 1501), where an activated state of the PTOL 1506 in the presence of the acid 1503 can emit more strongly at a different wavelength than when the PTOL 1501 is not in the presence of the acid 1503. A PTOL microscope could image the acid transformed PTOLs 1506 or the nontransformed PTOLs 1501 as a latent image on the resist. This in turn could provide a measure of the exposure properties and profiles at the resolution of the PTOL localization length scale.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not limiting.

A number of implementations have been described. Nevertheless, it will be understood that various modifications may be made. Accordingly, other implementations are within the scope of the following claims.

What is claimed is:

1. A method comprising:
    providing activation radiation to a sample, wherein the sample includes phototransformable optical labels ("PTOLs") distributed in the sample such that separation distances between PTOLs are less than a diffraction limited resolution of a detection objective of imaging optics used to image radiation from the PTOLs, to activate a subset of the PTOLs in the sample;
    providing excitation radiation to the sample to excite at least some of the activated subset of PTOLs;
    detecting, with the imaging optics, radiation emitted from the activated and excited PTOLs within the subset of PTOLs;
    controlling the activation radiation such that adjacent activated PTOLs in a focal plane of the detection objective of the imaging optics are separated by distances that are, on average, larger than the diffraction limited resolution of the detection objective;
    determining locations of the PTOLs based on the detected radiation; and
    creating a superresolution image of the sample based on the determined locations of the PTOLs.

2. The method of claim 1, wherein the detecting includes detecting radiation emitted from the subset of PTOLs with a position-sensitive detector located at an image plane of the PTOLs from which radiation is emitted.

3. The method of claim 1, further comprising providing deactivation radiation to the sample to deactivate PTOLs in the subset of PTOLs.

4. The method of claim 3, wherein the deactivation radiation includes sufficient excitation radiation to photobleach PTOLs in the subset of PTOLs.

5. The method of claim 1, wherein the activation radiation has an activation wavelength and wherein the excitation radiation has an excitation wavelength that is longer than the activation wavelength.

6. The method of claim 1, further comprising providing at least one of the activation radiation and the excitation radiation to the sample by total internal reflection of the at least one of the activation radiation and the excitation radiation at an interface between the sample and a substrate.

7. The method of claim 1, wherein the imaging optics include an objective lens through which the detected radiation is transmitted from the sample to a detector, and the method further comprising providing at least one of the activation radiation and the excitation radiation to the sample by transmitting the at least one of the activation radiation and the excitation radiation through the objective lens.

8. The method of claim 1, further comprising providing at least one of the activation radiation and the excitation radiation to the sample in the form of an optical lattice.

9. The method of claim 8, wherein the sample spans a plurality of lattice planes, and the method further comprising selectively detecting radiation emitted from PTOLs located in different lattice planes.

10. The method of claim 1, further comprising providing at least one of the activation radiation and the excitation radiation over a wide field.

11. The method of claim 1, wherein providing the activation radiation to the sample includes activating PTOLs in the subset of PTOLs in the sample through a multi-photon absorption process.

12. The method of claim 1, wherein providing the excitation radiation to the sample includes exciting PTOLs in the subset of PTOLs in the sample through a multi-photon absorption process.

13. The method of claim 1,
    wherein the imaging optics include an objective lens,
    wherein detecting radiation emitted from the activated and excited PTOLs includes detecting the emitted radiation with a position-sensitive detector, and
    wherein a magnification of the imaging optics and sizes of pixels in the position-sensitive detector are selected such that images of PTOLs fall on multiple pixels of the position-sensitive detector.

14. The method of claim 1, further comprising modulating the activation radiation that is provided to the sample to activate different subsets of activated PTOLs.

15. The method of claim 1, wherein the sample includes at least a first species and a second species of PTOL, and the method further comprising:
    distinguishing the first species from the second species based on at least one of emission characteristics of the first and second species and excitation characteristics of the first and second species.

16. The method of claim 1, wherein the PTOLs include fluorescent proteins.

17. The method of claim 1,
    wherein providing activation radiation to the sample includes providing the activation radiation to the sample to activate a plurality of different subsets of the PTOLs, wherein the different subsets of the optical labels are activated at different times,
    wherein providing the excitation radiation to the sample includes providing the excitation radiation to the sample to excite at least some of the PTOLs in the different activated subsets,
    wherein controlling the activation radiation includes controlling the activation radiation such that adjacent activated PTOLs in each of the different subsets are separated by distances that are, on average, larger than the diffraction limited resolution of the detection objective,
    wherein detecting the radiation includes detecting radiation emitted from the activated and excited PTOLs within the different subset of PTOLs, wherein radiation from the PTOLs within the different subsets is detected at different times,
    wherein determining locations of the PTOLs includes determining locations of PTOLs in different ones of the subsets based on the detected radiation, and
    wherein creating the superresolution image is further based on the determined locations of the PTOLs belonging to the different subsets.

18. An apparatus comprising:
    a position-sensitive detector adapted for detecting intensities of radiation as a function of position on the detector;

an optical system adapted for imaging light emitted from phototransformable optical labels ("PTOLs") in a sample onto the position sensitive-detector, wherein the PTOLs are distributed in the sample such that separation distances between the PTOLs are less than a diffraction limited resolution of a detection objection of the optical system;

a first light source adapted to provide first activation radiation to the sample to activate a subset of the PTOLs;

a second light source adapted to provide excitation radiation to the sample to excite a least some of the activated PTOLs within the subset of the PTOLs;

a controller adapted to control the activation radiation provided to the sample such that adjacent activated PTOLs in a focal plane of the detection objective of the optical system are separated by distances that are, on average, larger than the diffraction limited resolution of the detection objective;

at least one processor adapted to determine locations of activated and excited PTOLs with a sub-diffraction-limited accuracy based on position-dependent intensity data provided by the detector about radiation emitted from activated and excited PTOLs and adapted to generate a sub-diffraction-limited image based on the determined locations.

19. The apparatus of claim 18, wherein the first light source is adapted to provide activation radiation to the sample to activate a plurality of different subsets of the PTOLs at different times, wherein the second light source is adapted to provide the excitation radiation to the sample to excite at least some of the PTOLs in the different activated subsets, wherein the controller is adapted to control the activation radiation such that adjacent activated PTOLs in each of the different subsets are separated by distances that are, on average, larger than the diffraction limited resolution of the detection objective, wherein the detector is adapted to detect radiation emitted from the activated and excited PTOLs within the different subset of PTOLs at different times, wherein the at least one processor is adapted to determine in different ones of the subsets based on the detected radiation and to create the superresolution image based on the determined locations of the PTOLs belonging to the different subsets.

20. The apparatus of claim 18, wherein the controller is further adapted to control the excitation radiation provided to the sample, such that activated and excited PTOLs are deactivated through photobleaching by the excitation radiation.

21. The apparatus of claim 18, further comprising a third light source adapted to provide second activation radiation to the sample to activate a second subset of the PTOLs in the sample, wherein the second activation radiation has a wavelength that is different than a wavelength of the first activation radiation, and wherein PTOLs in the first and second subsets are different species of PTOL and emit radiation having different wavelengths.

22. The apparatus of claim 21, further comprising a filter located between the sample and the detector for discrimination particular wavelengths of radiation emitted from a species of PTOL.

23. The apparatus of claim 18, wherein the first activating radiation is provided to the sample through the detection objective.

24. The apparatus of claim 18, wherein a magnification of the optical system and sizes of pixels in the position-sensitive detector are selected such that images of PTOLs fall on multiple pixels of the position-sensitive detector.

25. The apparatus of claim 18, further comprising a shutter adapted to modulate the activation radiation provided to the sample.

26. The apparatus of claim 18, wherein the sample includes a cell and wherein the PTOLs include fluorescent proteins that are genetically expressed within the cell.

27. The apparatus of claim 26, wherein the fluorescent proteins are genetically expressed within the cell due to the insertion of DNA plasmids into the cell.

28. The apparatus of claim 18, wherein the sample includes a cell and wherein the PTOLs include a plurality of species of fluorescent proteins, wherein each species binds to different specific proteins in the cell.

* * * * *